US012588937B2

(12) United States Patent　　　　　　(10) Patent No.:　US 12,588,937 B2
Davison et al.　　　　　　　　　　　　　 (45) Date of Patent:　　Mar. 31, 2026

(54) VOLAR DISTAL RADIUS STABILIZATION SYSTEM

(71) Applicant: GLOBUS MEDICAL, INC., Audubon, PA (US)

(72) Inventors: Andrew Davison, Downingtown, PA (US); Stephanie Wolfe, Perkasie, PA (US); Evan Langdale, Philadelphia, PA (US); Joseph DePaul, Lansdale, PA (US); Barclay Davis, Glenmoore, PA (US); Gabrielle Zingalis, Philadelphia, PA (US); Michelle Gray, Oley, PA (US); David Laird, Jr., Birdsboro, PA (US)

(73) Assignee: Globus Medical, Inc., Audubon, PA (US)

( * ) Notice: Subject to any disclaimer, the term of this patent is extended or adjusted under 35 U.S.C. 154(b) by 113 days.

(21) Appl. No.: 18/739,478

(22) Filed: Jun. 11, 2024

(65) Prior Publication Data

US 2024/0325061 A1　　Oct. 3, 2024

Related U.S. Application Data

(63) Continuation of application No. 17/506,229, filed on Oct. 20, 2021, now Pat. No. 12,004,790, which is a
(Continued)

(51) Int. Cl.
| | |
|---|---|
| *A61B 17/80* | (2006.01) |
| *A61B 17/04* | (2006.01) |
| *A61B 17/17* | (2006.01) |
| *A61B 17/88* | (2006.01) |
| *B29C 70/46* | (2006.01) |

(52) U.S. Cl.
CPC ...... *A61B 17/8085* (2013.01); *A61B 17/0401* (2013.01); *A61B 17/1728* (2013.01); *A61B 17/1782* (2016.11); *A61B 17/80* (2013.01); *A61B 17/8014* (2013.01); *A61B 17/8042* (2013.01); *A61B 17/8057* (2013.01); *A61B 17/8061* (2013.01); *A61B 17/808* (2013.01);
(Continued)

(58) Field of Classification Search
CPC ................................................. A61B 17/8085
See application file for complete search history.

(56) References Cited

U.S. PATENT DOCUMENTS

| | | | |
|---|---|---|---|
| 1,105,105 | A | 7/1914 | Sherman |
| 2,486,303 | A | 10/1949 | Longfellow |
(Continued)

FOREIGN PATENT DOCUMENTS

| | | |
|---|---|---|
| CN | 201987653 U | 9/2011 |
| CN | 202313691 U | 7/2012 |
(Continued)

*Primary Examiner* — Christian A Sevilla

(57) ABSTRACT

Devices, systems, and methods for bone stabilization, especially volar distal radius stabilization. The stabilization system may include a bone plate having an elongated portion, an enlarged head portion, and a transition region connecting the elongated portion to the enlarged head portion, and the plate including a plurality of through holes. A plurality of fasteners may be configured to extend through one or more of the plurality of through holes in the bone plate and into the bone. The plate may be used to stabilize a fracture in a long bone, such as a radius.

17 Claims, 27 Drawing Sheets

Related U.S. Application Data continuation of application No. 16/539,492, filed on Aug. 13, 2019, now Pat. No. 11,160,590, which is a continuation of application No. 15/456,642, filed on Mar. 13, 2017, now Pat. No. 10,420,596, which is a continuation-in-part of application No. 15/238,773, filed on Aug. 17, 2016, now Pat. No. 10,383,668.

(52) U.S. Cl.
  CPC ........ *A61B 17/809* (2013.01); *A61B 17/8897* (2013.01); *B29C 70/46* (2013.01)

(56) References Cited

U.S. PATENT DOCUMENTS

| | | | |
|---|---|---|---|
| 3,716,050 A * | 2/1973 | Johnston | ............ A61B 17/8061 |
| | | | 606/286 |
| 4,493,317 A | 1/1985 | Klaue | |
| 4,524,765 A | 6/1985 | de Zbikowski | |
| 4,651,724 A | 3/1987 | Berentey et al. | |
| 4,683,878 A | 8/1987 | Carter | |
| 4,781,183 A | 11/1988 | Casey et al. | |
| 4,867,144 A | 9/1989 | Karas et al. | |
| 5,002,544 A | 3/1991 | Klaue et al. | |
| 5,041,114 A | 8/1991 | Chapman et al. | |
| 5,151,103 A | 9/1992 | Tepic et al. | |
| 5,259,398 A | 11/1993 | Vrespa | |
| 5,364,399 A | 11/1994 | Lowery et al. | |
| 5,372,598 A | 12/1994 | Luhr et al. | |
| 5,423,826 A | 6/1995 | Coates et al. | |
| 5,601,553 A | 2/1997 | Trebing et al. | |
| 5,676,667 A | 10/1997 | Hausman | |
| 5,709,686 A | 1/1998 | Talos et al. | |
| 5,718,704 A | 2/1998 | Medoff | |
| 5,746,742 A | 5/1998 | Runciman et al. | |
| 5,785,712 A | 7/1998 | Runciman et al. | |
| 5,938,664 A | 8/1999 | Winquist et al. | |
| 6,001,099 A | 12/1999 | Huebner | |
| 6,017,345 A | 1/2000 | Richelsoph | |
| 6,096,040 A | 8/2000 | Esser | |
| 6,152,927 A | 11/2000 | Farris et al. | |
| 6,206,881 B1 | 3/2001 | Frigg et al. | |
| 6,283,969 B1 | 9/2001 | Grusin et al. | |
| 6,309,393 B1 | 10/2001 | Tepic et al. | |
| 6,322,562 B1 | 11/2001 | Wolter | |
| 6,364,882 B1 | 4/2002 | Orbay | |
| 6,533,786 B1 | 3/2003 | Needham et al. | |
| 6,623,486 B1 | 9/2003 | Weaver et al. | |
| 6,669,700 B1 | 12/2003 | Farris et al. | |
| 6,669,701 B2 | 12/2003 | Steiner et al. | |
| 6,712,820 B2 | 3/2004 | Orbay | |
| 6,719,759 B2 | 4/2004 | Wagner et al. | |
| 6,730,091 B1 | 5/2004 | Pfefferle et al. | |
| 6,866,665 B2 | 3/2005 | Orbay | |
| 6,955,677 B2 | 10/2005 | Dahners | |
| 6,974,461 B1 | 12/2005 | Wolter | |
| 7,001,387 B2 | 2/2006 | Farris et al. | |
| 7,063,701 B2 | 6/2006 | Michelson | |
| 7,128,744 B2 | 10/2006 | Weaver et al. | |
| 7,137,987 B2 | 11/2006 | Patterson et al. | |
| 7,153,309 B2 | 12/2006 | Huebner et al. | |
| 7,179,260 B2 | 2/2007 | Gerlach et al. | |
| 7,250,053 B2 | 7/2007 | Orbay | |
| 7,294,130 B2 | 11/2007 | Orbay | |
| 7,322,983 B2 | 1/2008 | Harris | |
| 7,341,589 B2 | 3/2008 | Weaver et al. | |
| 7,354,441 B2 | 4/2008 | Frigg | |
| 7,604,657 B2 | 10/2009 | Orbay et al. | |
| 7,632,277 B2 | 12/2009 | Woll et al. | |
| 7,635,381 B2 | 12/2009 | Orbay | |
| 7,637,928 B2 | 12/2009 | Fernandez | |
| 7,655,029 B2 | 2/2010 | Niedernberger et al. | |
| 7,695,472 B2 | 4/2010 | Young | |
| 7,722,653 B2 | 5/2010 | Young et al. | |
| 7,740,648 B2 | 6/2010 | Young et al. | |
| 7,776,076 B2 | 8/2010 | Grady, Jr. et al. | |
| 7,857,838 B2 | 12/2010 | Orbay | |
| 7,867,260 B2 | 1/2011 | Meyer et al. | |
| 7,867,261 B2 | 1/2011 | Sixto, Jr. et al. | |
| 7,875,062 B2 | 1/2011 | Lindemann et al. | |
| 7,905,910 B2 | 3/2011 | Gerlach et al. | |
| 7,909,858 B2 | 3/2011 | Gerlach et al. | |
| 7,951,178 B2 | 5/2011 | Jensen | |
| 7,951,179 B2 | 5/2011 | Matityahu | |
| 7,976,570 B2 | 7/2011 | Wagner et al. | |
| D643,121 S | 8/2011 | Millford et al. | |
| D646,785 S | 10/2011 | Milford | |
| 8,043,297 B2 | 10/2011 | Grady, Jr. et al. | |
| 8,057,520 B2 | 11/2011 | Ducharme et al. | |
| 8,062,296 B2 | 11/2011 | Orbay et al. | |
| 8,100,953 B2 | 1/2012 | White et al. | |
| 8,105,367 B2 | 1/2012 | Austin et al. | |
| 8,114,081 B2 | 2/2012 | Kohut et al. | |
| 8,118,846 B2 | 2/2012 | Leither et al. | |
| 8,162,950 B2 | 4/2012 | Digeser et al. | |
| 8,167,918 B2 | 5/2012 | Strnad et al. | |
| 8,177,820 B2 | 5/2012 | Anapliotis et al. | |
| 8,246,661 B2 | 8/2012 | Beutter et al. | |
| 8,252,032 B2 | 8/2012 | White et al. | |
| 8,257,403 B2 | 9/2012 | Den Hartog et al. | |
| 8,257,405 B2 | 9/2012 | Haidukewych et al. | |
| 8,257,406 B2 | 9/2012 | Kay et al. | |
| 8,262,707 B2 | 9/2012 | Huebner et al. | |
| 8,267,972 B1 | 9/2012 | Gehlert | |
| 8,317,842 B2 | 11/2012 | Graham et al. | |
| 8,323,321 B2 | 12/2012 | Gradl | |
| 8,337,535 B2 | 12/2012 | White et al. | |
| 8,343,155 B2 | 1/2013 | Fisher et al. | |
| 8,382,807 B2 | 2/2013 | Austin et al. | |
| 8,394,098 B2 | 3/2013 | Orbay et al. | |
| 8,394,130 B2 | 3/2013 | Orbay et al. | |
| 8,398,685 B2 | 3/2013 | McGarity et al. | |
| 8,403,966 B2 | 3/2013 | Ralph et al. | |
| 8,419,775 B2 | 4/2013 | Orbay et al. | |
| 8,435,272 B2 | 5/2013 | Dougherty et al. | |
| 8,439,918 B2 | 5/2013 | Gelfand | |
| 8,444,679 B2 | 5/2013 | Ralph et al. | |
| 8,491,593 B2 | 7/2013 | Prien et al. | |
| 8,506,608 B2 | 8/2013 | Cerynik et al. | |
| 8,512,385 B2 | 8/2013 | White et al. | |
| 8,518,090 B2 | 8/2013 | Huebner et al. | |
| 8,523,862 B2 | 9/2013 | Murashko, Jr. | |
| 8,523,919 B2 | 9/2013 | Huebner et al. | |
| 8,523,921 B2 | 9/2013 | Horan et al. | |
| 8,551,095 B2 | 10/2013 | Fritzinger et al. | |
| 8,568,462 B2 | 10/2013 | Sixto, Jr. et al. | |
| 8,574,268 B2 | 11/2013 | Chan et al. | |
| 8,597,334 B2 | 12/2013 | Mocanu | |
| 8,603,147 B2 | 12/2013 | Sixto, Jr. et al. | |
| 8,617,224 B2 | 12/2013 | Kozak et al. | |
| 8,632,574 B2 | 1/2014 | Kortenbach et al. | |
| 8,641,741 B2 | 2/2014 | Murashko, Jr. | |
| 8,641,744 B2 | 2/2014 | Weaver et al. | |
| 8,663,224 B2 | 3/2014 | Overes et al. | |
| 8,728,082 B2 | 5/2014 | Fritzinger et al. | |
| 8,728,126 B2 | 5/2014 | Steffen | |
| 8,740,905 B2 | 6/2014 | Price et al. | |
| 8,747,442 B2 | 6/2014 | Orbay et al. | |
| 8,764,751 B2 | 7/2014 | Orbay et al. | |
| 8,764,808 B2 | 7/2014 | Gonzalez-Hernandez | |
| 8,777,998 B2 | 7/2014 | Daniels et al. | |
| 8,790,376 B2 | 7/2014 | Fritzinger et al. | |
| 8,790,377 B2 | 7/2014 | Ralph et al. | |
| 8,808,333 B2 | 8/2014 | Kuster et al. | |
| 8,808,334 B2 | 8/2014 | Strnad et al. | |
| 8,834,532 B2 | 9/2014 | Velikov et al. | |
| 8,834,537 B2 | 9/2014 | Castanada et al. | |
| 8,852,246 B2 | 10/2014 | Hansson | |
| 8,852,249 B2 | 10/2014 | Ahrens et al. | |
| 8,864,802 B2 | 10/2014 | Schwager et al. | |
| 8,870,931 B2 | 10/2014 | Dahners et al. | |
| 8,888,825 B2 | 11/2014 | Batsch et al. | |
| 8,906,076 B2 | 12/2014 | Mocanu et al. | |
| 8,911,482 B2 | 12/2014 | Lee et al. | |

(56) References Cited

U.S. PATENT DOCUMENTS

| | | | |
|---|---|---|---|
| 8,915,918 B2 | 12/2014 | Graham et al. |
| 8,926,675 B2 | 1/2015 | Leung et al. |
| 8,940,026 B2 | 1/2015 | Hilse et al. |
| 8,940,028 B2 | 1/2015 | Austin et al. |
| 8,940,029 B2 | 1/2015 | Leung et al. |
| 8,951,291 B2 | 2/2015 | Impellizzeri |
| 8,968,368 B2 | 3/2015 | Tepic |
| 9,011,457 B2 | 4/2015 | Grady, Jr. et al. |
| 9,023,052 B2 | 5/2015 | Lietz et al. |
| 9,050,151 B2 | 6/2015 | Schilter |
| 9,072,555 B2 | 7/2015 | Michel |
| 9,072,557 B2 | 7/2015 | Fierlbeck et al. |
| 9,107,678 B2 | 8/2015 | Murner et al. |
| 9,107,711 B2 | 8/2015 | Hainard |
| 9,107,713 B2 | 8/2015 | Horan et al. |
| 9,107,718 B2 | 8/2015 | Isch |
| 9,113,970 B2 | 8/2015 | Lewis et al. |
| 9,149,310 B2 | 10/2015 | Fritzinger et al. |
| 9,161,791 B2 | 10/2015 | Frigg |
| 9,161,795 B2 | 10/2015 | Chasbrummel et al. |
| 9,168,075 B2 | 10/2015 | Dell'Oca |
| 9,179,950 B2 | 11/2015 | Zajac et al. |
| 9,179,956 B2 | 11/2015 | Cerynik et al. |
| 9,180,020 B2 | 11/2015 | Gause et al. |
| 9,211,151 B2 | 12/2015 | Weaver et al. |
| 9,259,217 B2 | 2/2016 | Fritzinger et al. |
| 9,259,255 B2 | 2/2016 | Lewis et al. |
| 9,271,769 B2 | 3/2016 | Batsch et al. |
| 9,283,010 B2 | 3/2016 | Medoff et al. |
| 9,295,506 B2 | 3/2016 | Raven, III et al. |
| 9,314,284 B2 | 4/2016 | Chan et al. |
| 9,320,554 B2 | 4/2016 | Greenberg et al. |
| 9,322,562 B2 | 4/2016 | Takayama et al. |
| 9,370,388 B2 | 6/2016 | Globerman et al. |
| 9,433,407 B2 | 9/2016 | Fritzinger et al. |
| 9,433,452 B2 | 9/2016 | Weiner et al. |
| 9,468,479 B2 | 10/2016 | Marotta et al. |
| 9,480,512 B2 | 11/2016 | Orbay |
| 9,486,262 B2 | 11/2016 | Andermahr et al. |
| 9,492,213 B2 * | 11/2016 | Orbay ................ A61B 17/8042 |
| 9,510,878 B2 | 12/2016 | Nanavati et al. |
| 9,510,880 B2 | 12/2016 | Terrill et al. |
| 9,526,543 B2 | 12/2016 | Castaneda et al. |
| 9,545,277 B2 | 1/2017 | Wolf et al. |
| 9,566,097 B2 * | 2/2017 | Fierlbeck ........... A61B 17/8061 |
| 9,636,157 B2 | 5/2017 | Medoff |
| 9,649,141 B2 * | 5/2017 | Raven, III ............. A61B 17/56 |
| 9,668,794 B2 | 6/2017 | Kuster et al. |
| 2002/0045901 A1 | 4/2002 | Wagner et al. |
| 2004/0097937 A1 | 5/2004 | Pike et al. |
| 2004/0102775 A1 | 5/2004 | Huebner |
| 2005/0085818 A1 | 4/2005 | Huebner |
| 2005/0107796 A1 | 5/2005 | Gerlach et al. |
| 2005/0131413 A1 | 6/2005 | O'Driscoll et al. |
| 2005/0187551 A1 | 8/2005 | Orbay et al. |
| 2006/0009771 A1 | 1/2006 | Orbay et al. |
| 2006/0149265 A1 | 7/2006 | James et al. |
| 2006/0173458 A1 | 8/2006 | Forstein et al. |
| 2006/0241607 A1 | 10/2006 | Myerson et al. |
| 2007/0270849 A1 | 11/2007 | Orbay et al. |
| 2007/0270850 A1 | 11/2007 | Geissler |
| 2008/0021477 A1 | 1/2008 | Strnad et al. |
| 2008/0234677 A1 | 9/2008 | Dahners et al. |
| 2008/0234749 A1 | 9/2008 | Forstein |
| 2008/0275510 A1 | 11/2008 | Schonhardt et al. |
| 2009/0012571 A1 | 1/2009 | Perrow et al. |
| 2009/0024172 A1 | 1/2009 | Pizzicara |
| 2009/0024173 A1 | 1/2009 | Reis, Jr. |
| 2009/0118773 A1 | 5/2009 | James et al. |
| 2009/0198285 A1 | 8/2009 | Raven, III |
| 2009/0204121 A1 | 8/2009 | Cavallazzi et al. |
| 2009/0228010 A1 | 9/2009 | Gonzalez-Hernandez et al. |
| 2009/0228047 A1 * | 9/2009 | Derouet ............. A61B 17/1782 |
| | | 606/301 |
| 2009/0248084 A1 | 10/2009 | Hintermann |
| 2009/0281543 A1 | 11/2009 | Orbay et al. |
| 2009/0312760 A1 | 12/2009 | Forstein et al. |
| 2010/0030276 A1 | 2/2010 | Huebner et al. |
| 2010/0057086 A1 | 3/2010 | Price et al. |
| 2010/0114097 A1 | 5/2010 | Siravo et al. |
| 2010/0121326 A1 | 5/2010 | Woll et al. |
| 2010/0274247 A1 | 10/2010 | Grady, Jr. et al. |
| 2011/0106086 A1 | 5/2011 | Laird |
| 2011/0218580 A1 | 9/2011 | Schwager et al. |
| 2011/0276097 A1 | 11/2011 | Raven, III et al. |
| 2012/0059424 A1 | 3/2012 | Epperly et al. |
| 2012/0165878 A1 | 6/2012 | Hwa et al. |
| 2012/0323284 A1 | 12/2012 | Baker et al. |
| 2013/0018426 A1 | 1/2013 | Tsai et al. |
| 2013/0046349 A1 | 2/2013 | Medoff et al. |
| 2013/0060291 A1 | 3/2013 | Petersheim |
| 2013/0123841 A1 | 5/2013 | Lyon |
| 2013/0138156 A1 | 5/2013 | Derouet |
| 2013/0150902 A1 | 6/2013 | Leite |
| 2013/0165981 A1 | 6/2013 | Clasbrummet et al. |
| 2013/0211463 A1 | 8/2013 | Mizuno et al. |
| 2014/0005728 A1 | 1/2014 | Koay et al. |
| 2014/0018862 A1 | 1/2014 | Koay et al. |
| 2014/0031879 A1 | 1/2014 | Sixto, Jr. et al. |
| 2014/0066996 A1 | 3/2014 | Price et al. |
| 2014/0094856 A1 | 4/2014 | Sinha |
| 2014/0121710 A1 | 5/2014 | Weaver et al. |
| 2014/0180345 A1 | 6/2014 | Chan et al. |
| 2014/0277178 A1 | 9/2014 | O'Kane et al. |
| 2014/0277181 A1 | 9/2014 | Garlock |
| 2014/0316473 A1 | 10/2014 | Pfeffer |
| 2014/0330320 A1 | 11/2014 | Wolter |
| 2014/0378975 A1 | 12/2014 | Castaneda et al. |
| 2015/0051650 A1 | 2/2015 | Verstreken et al. |
| 2015/0051651 A1 | 2/2015 | Terrill et al. |
| 2015/0073486 A1 | 3/2015 | Marotta et al. |
| 2015/0105829 A1 | 4/2015 | Laird |
| 2015/0112355 A1 | 4/2015 | Dahners et al. |
| 2015/0134011 A1 | 5/2015 | Medoff |
| 2015/0142065 A1 | 5/2015 | Schonhardt et al. |
| 2015/0190185 A1 | 7/2015 | Koay et al. |
| 2015/0209091 A1 | 7/2015 | Sixto, Jr. et al. |
| 2015/0216571 A1 | 8/2015 | Impellizzeri |
| 2015/0223852 A1 | 8/2015 | Lietz et al. |
| 2015/0272638 A1 | 10/2015 | Langford |
| 2015/0282851 A1 | 10/2015 | Michel |
| 2015/0313653 A1 | 11/2015 | Ponce et al. |
| 2015/0313654 A1 | 11/2015 | Horan et al. |
| 2015/0327898 A1 | 11/2015 | Martin |
| 2015/0351816 A1 | 12/2015 | Lewis et al. |
| 2016/0022336 A1 | 1/2016 | Bateman |
| 2016/0030035 A1 | 2/2016 | Zajac et al. |
| 2016/0045237 A1 | 2/2016 | Cerynik et al. |
| 2016/0045238 A1 | 2/2016 | Bohay et al. |
| 2016/0074081 A1 | 3/2016 | Weaver et al. |
| 2016/0166297 A1 | 6/2016 | Mighell et al. |
| 2016/0166298 A1 | 6/2016 | Mighell et al. |
| 2016/0220286 A1 | 8/2016 | Garvey et al. |
| 2016/0262814 A1 | 9/2016 | Wainscott |
| 2016/0278828 A1 | 9/2016 | Ragghianti |
| 2016/0310183 A1 | 10/2016 | Shaw et al. |
| 2016/0310185 A1 | 10/2016 | Sixto et al. |
| 2016/0324552 A1 | 11/2016 | Baker et al. |
| 2016/0354122 A1 | 12/2016 | Montello et al. |
| 2017/0035478 A1 | 2/2017 | Andermahr et al. |
| 2017/0042592 A1 | 2/2017 | Kim |
| 2017/0042596 A9 | 2/2017 | Mighell et al. |
| 2017/0049493 A1 | 2/2017 | Gauneau et al. |
| 2017/0065312 A1 | 3/2017 | Lauf et al. |
| 2017/0215931 A1 | 8/2017 | Cremer et al. |
| 2018/0049787 A1 | 2/2018 | Davison et al. |
| 2018/0049788 A1 | 2/2018 | Rutledge et al. |
| 2019/0328431 A1 | 10/2019 | Davison et al. |

FOREIGN PATENT DOCUMENTS

| | | |
|---|---|---|
| CN | 202821574 U | 3/2013 |
| CN | 202821575 U | 3/2013 |
| CN | 203506858 U | 4/2014 |

(56)  References Cited

FOREIGN PATENT DOCUMENTS

| | | | |
|---|---|---|---|
| CN | 203815563 | U | 9/2014 |
| CN | 105982727 | A | 10/2016 |
| EP | 0374084 | B1 | 6/1990 |
| EP | 2476388 | B1 | 7/2012 |
| EP | 3284427 | A1 | 2/2018 |
| FR | 2472373 | A1 | 7/1981 |
| FR | 2846870 | A1 | 5/2004 |
| FR | 2928259 | A1 | 9/2009 |
| JP | 2003210478 | A | 7/2003 |
| JP | 2007-083046 | A | 4/2007 |
| JP | 2008-132365 | A | 6/2008 |
| JP | 2014046200 | A | 3/2014 |
| JP | 2014-226523 | A | 12/2014 |
| JP | 2018525164 | A | 9/2018 |
| TW | 201316942 | A | 5/2013 |
| WO | 2012050424 | A1 | 4/2012 |
| WO | 2016079504 | A1 | 5/2016 |
| WO | 2017035302 | A1 | 3/2017 |

* cited by examiner

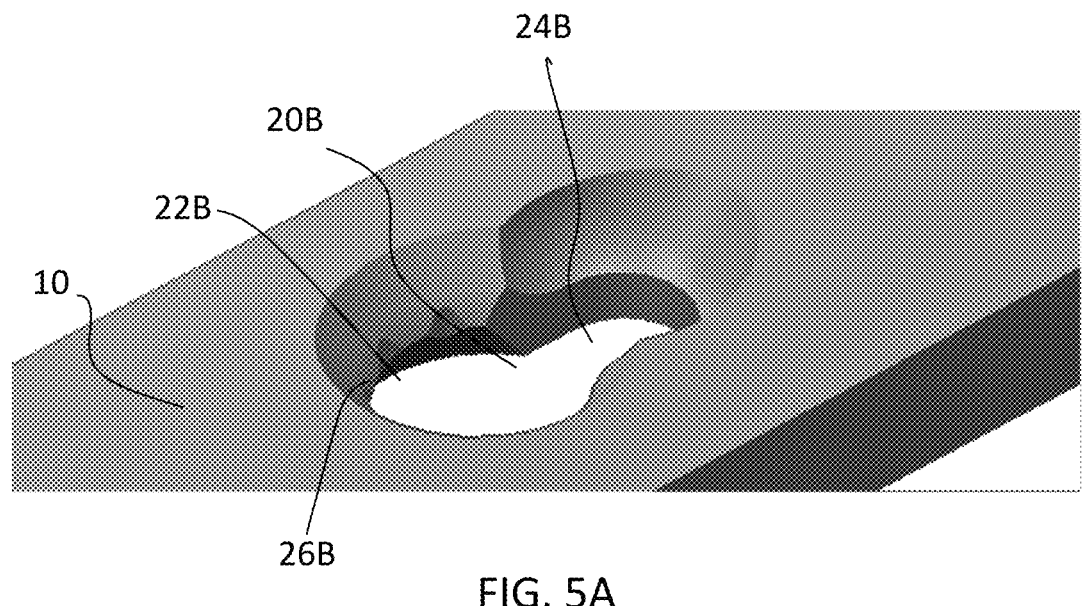
FIG. 5A
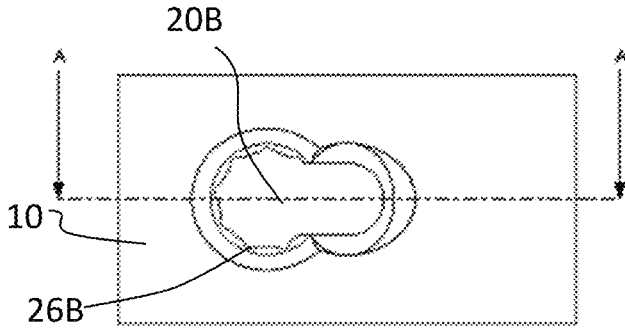
FIG. 5B
FIG. 5C

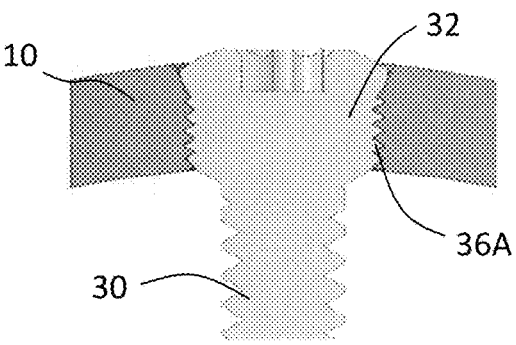
FIG. 11A
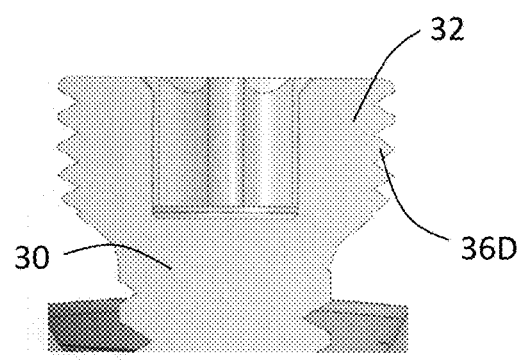
FIG. 11B
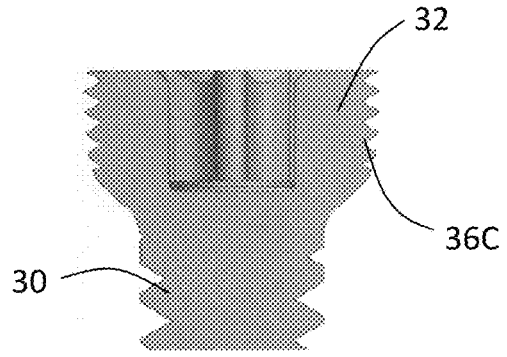
FIG. 11C
FIG. 11D
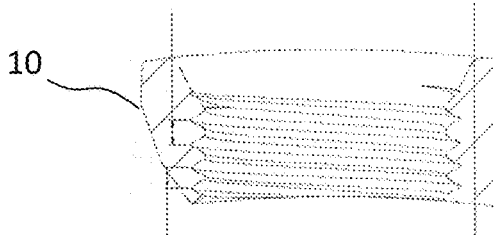
FIG. 11E

16

20

28

10

26

29

20

28

10

26

29

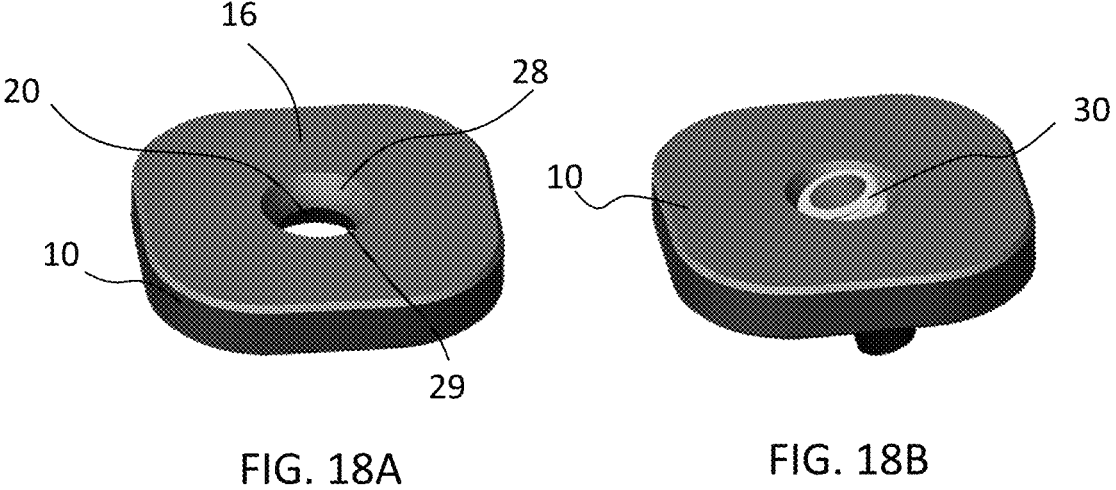
FIG. 18A                    FIG. 18B
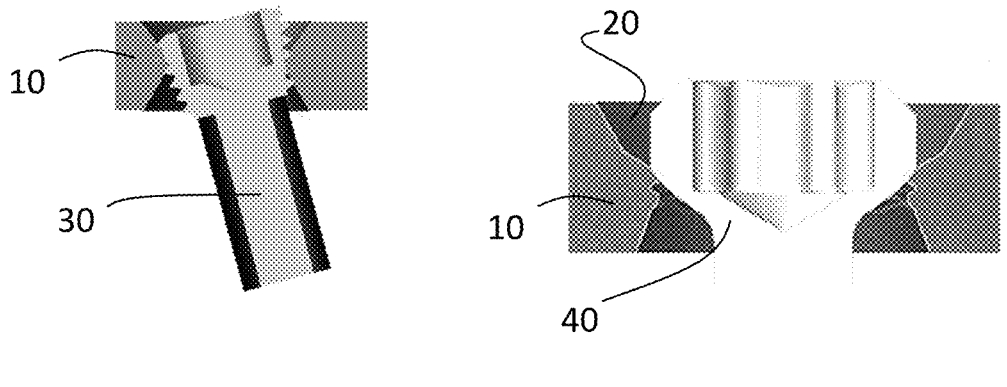
FIG. 18C                    FIG. 18D

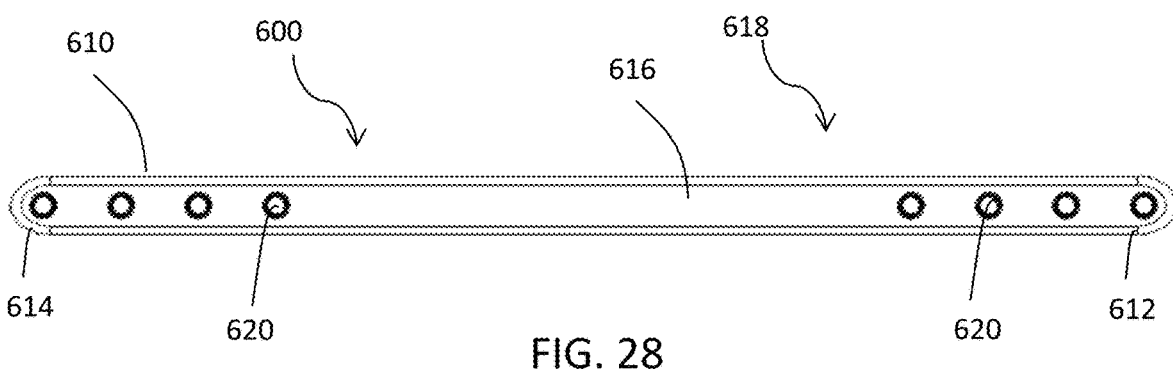
FIG. 28
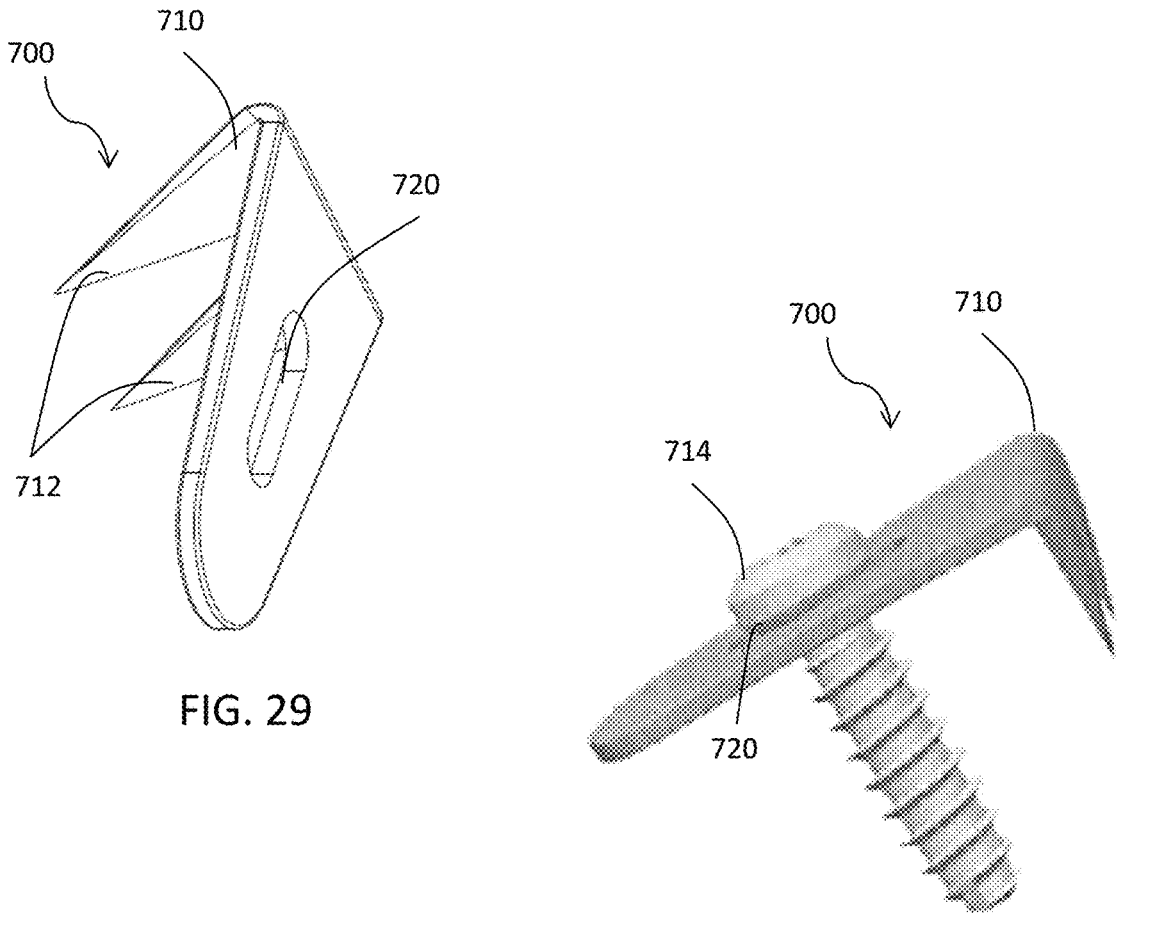
FIG. 29
FIG. 30

VOLAR DISTAL RADIUS STABILIZATION SYSTEM

CROSS REFERENCE TO RELATED APPLICATIONS

The present application is a continuation of U.S. patent application Ser. No. 17/506,229, filed on Oct. 20, 2021, which is a continuation of U.S. patent application Ser. No. 16/539,492, filed on Aug. 13, 2019, which is a continuation of U.S. patent application Ser. No. 15/456,642, filed on Mar. 13, 2017, which is a continuation-in-Part of U.S. patent application Ser. No. 15/238,773, filed on Aug. 17, 2016, the contents of which are incorporated herein in their entirety by reference for all purposes.

FIELD

The present disclosure relates to surgical devices and stabilization systems, for example, for trauma applications, and more particularly, for stabilization of volar distal radius fractures.

BACKGROUND

Bone fractures are often repaired by internal fixation of the bone, such as diaphyseal bone, using one or more plates. The plate is held against the fractured bone with screws, for example, which engage the bone and heads which provide a compressive force against the plate. The plate and bone are thus forced against each other in a manner that transfers load primarily between a bone contacting surface of the plate and the bone surface to reinforce the fractured bone during healing. This manner of plating generally creates relatively low stress concentration in the bone, as there may be a large contact area between the plate and the diaphyseal bone surface permitting transfer of load to be dispersed. There may be a desire to use locking screws, non-locking screws, or a combination of both that are able to dynamically compress the bone. Of course, the designs of the plates, types of screws, and locking and/or non-locking capabilities may vary based on the location and type of fracture.

The three long bones of the upper extremity are the humerus, radius, and ulna. In the case of radial fracture fixation, a volar approach may be suitable for plating certain fracture types. There remains a need, however, for improved plating systems for anatomical articular reduction and stable fixation of the radius.

SUMMARY

To meet this and other needs, devices, systems, and methods of bone stabilization are provided, for example, for radius stabilization. The volar distal radius stabilization systems may include one or more plates and one or more fasteners. Although generally described with reference to the radius, it will be appreciated that the stabilization systems described herein may be used or adapted to be used for the fixation of other long bones as well, such as the humerus, femur, tibia, etc.

According to one embodiment, a stabilization system includes a bone plate and a plurality of fasteners. The bone plate comprises an elongated portion extending along a longitudinal axis, an enlarged head portion, and a transition region connecting the elongated portion to the enlarged head portion, wherein the transition region is curved and connect to an end portion of the enlarged head portion, the bone plate comprising a plurality of through holes extending through the enlarged head portion, the transition region, and the elongated portion. The fasteners are configured to extend through one or more of the plurality of through holes in the bone plate and configured to secure the bone plate to the bone.

The fasteners may include locking fasteners (e.g., configured to lock to the plate), non-locking fasteners (e.g., configured to provide dynamic compression of the bone), polyaxial fasteners (e.g., configured to be inserted at a plurality of angles or trajectories), fixed angle fasteners (e.g., configured to be inserted at a fixed angle or trajectory), or any other suitable fasteners known in the art.

In some instances, the locking fasteners may include fasteners having self-forming threads on a head portion of the fasteners, which are configured to lock to at least one of the plurality of through holes on the plate.

According to another embodiment, a stabilization system configured to stabilize a radius includes a bone plate, a plurality of fixed angle fasteners, a polyaxial fastener, and a fastener. The bone plate comprises an elongated portion extending along a longitudinal axis, an enlarged head portion, and a transition region connecting the elongated portion to the enlarged head portion, wherein the transition region is curved and connect to an end portion of the enlarged head portion, the bone plate comprising a plurality of fixed angle holes positioned in general alignment along the elongated portion, a polyaxial hole positioned proximate to the end portion of the enlarged head portion connected to the transition region, and an elongated slot on the elongated portion. The fixed angle fasteners are configured to be received in the fixed angle holes, the plurality of fixed angle fasteners configured to be aimed at a radio-carpal joint and a distal radio-ulnar joint. The polyaxial fastener is configured to be received in the polyaxial hole, the polyaxial fastener configured to be aimed at a radial styloid. The fastener is configured to be received in the elongated slot, wherein the elongated slot allows for proximal-distal and medial-lateral adjustment of the plate.

According to another embodiment, a stabilization system for stabilizing a bone includes a bone plate and a plurality of fasteners. The bone plate has an upper surface and a lower surface configured to contact the bone, wherein the lower surface comprises one or more recesses configured to reduce contact between the plate and a surface of the bone. The bone plate comprises an elongated portion extending along a longitudinal axis, an enlarged head portion, and a transition region connecting the elongated portion to the enlarged head portion, wherein the transition region is connect to an end portion of the enlarged head portion and the other end portion of the enlarged head portion is a free end, the bone plate comprising a plurality of through holes extending through the enlarged head portion, the transition region, and the elongated portion. The plurality of fasteners are configured to extend through one or more of the plurality of through holes in the bone plate and configured to secure the bone plate to the bone.

According to yet another embodiment, one or more methods of installing a stabilization system may include aligning a bone plate against the volar side of the radial bone, and inserting one or more fasteners through the bone plate and into the bone to stabilize the radius and repair the fracture.

Also provided are kits for the stabilization systems including bone plates of varying sizes and orientations, fasteners including locking fasteners, non-locking, compression fasteners, polyaxial fasteners, fixed angle fasteners, or any other suitable fasteners, drill guides, k-wires, and other components for installing the same.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIGS. 5A-5C show a perspective view, top view, and cross-section view, respectively, of an another embodiment of a combination hole;

FIGS. 11A-11E shows alternative locking screw and openings in plates according to yet another embodiment;

FIGS. 18A-18D depict a plate assembly according to one embodiment where a locking or non-locking fastener may be positioned at an angle or perpendicular to the plate;

FIG. 28 depicts a stabilization system according to one embodiment including a bridge bone plate;

FIG. 29 depicts a stabilization system according to one embodiment including a lunate facet hook plate;

FIG. 30 depicts the lunate facet hook plate of FIG. 29 with a fixation screw;

DETAILED DESCRIPTION

Figures 1A, 1B:
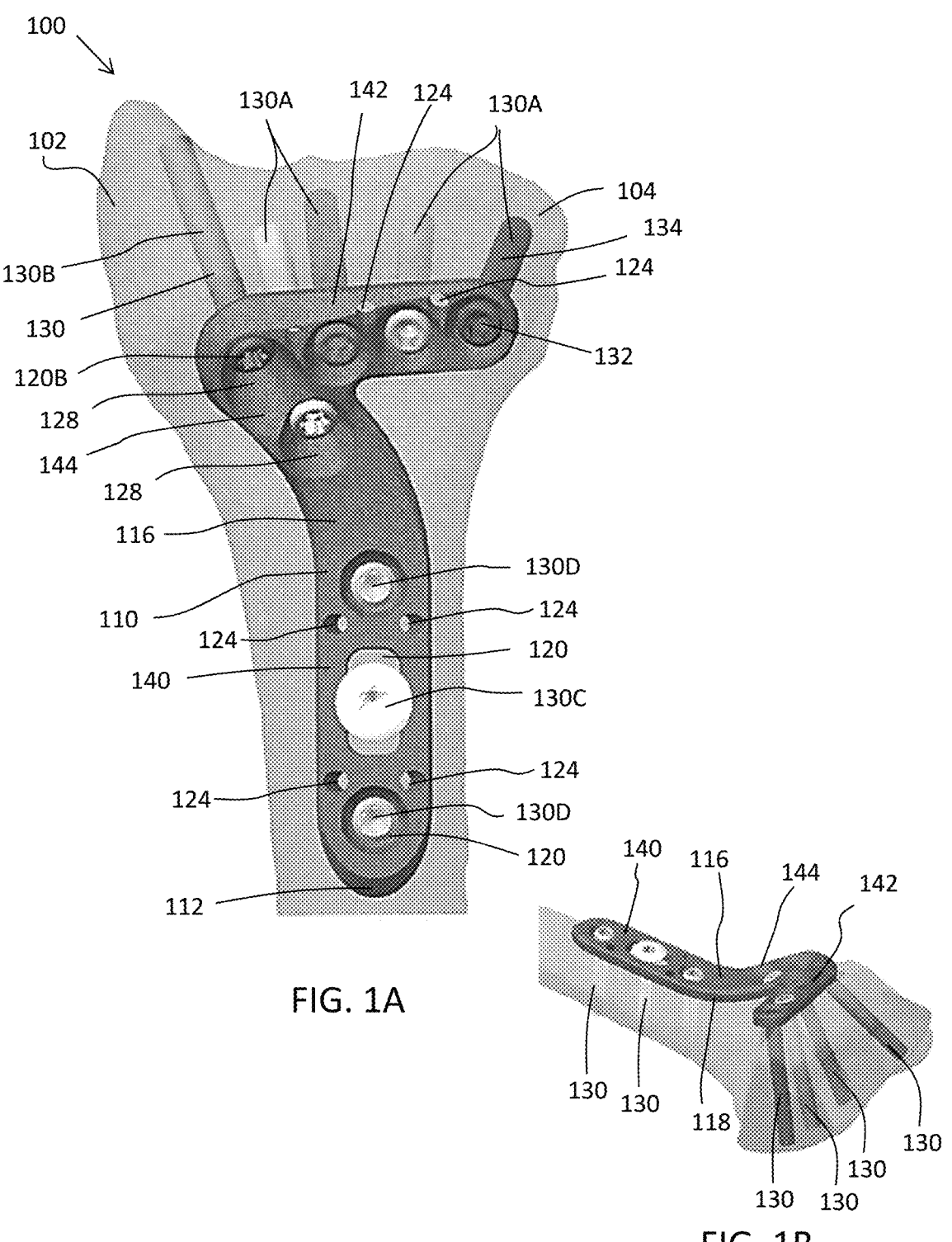
FIGS. 1A-1J depict stabilization systems according to embodiments including volar distal radius bone plates and a plurality of bone fasteners.

Embodiments of the disclosure are generally directed to devices, systems, and methods for bone stabilization, especially radius stabilization. Specifically, embodiments are directed to volar distal radius stabilization systems including a bone plate configured to sit against the volar side of the radial bone. The fasteners may be configured to secure the bone plate to the radius. Still other embodiments are directed to different types of holes and fasteners configured to provide locking and/or compression to the bone.

The bone plate may be comprised of titanium, stainless steel, cobalt chrome, carbon composite, plastic or polymer-such as polyetheretherketone (PEEK), polyethylene, ultra high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a body. Similarly, the fasteners may be comprised of titanium, cobalt chrome, cobalt-chrome-molybdenum, stainless steel, tungsten carbide, combinations or alloys of such materials or other appropriate biocompatible materials. Although the above list of materials includes many typical materials out of which bone plates and bone fasteners are made, it should be understood that the bone plates and fasteners comprised of any appropriate material are contemplated.

The embodiments of the disclosure and the various features and advantageous details thereof are explained more fully with reference to the non-limiting embodiments and examples that are described and/or illustrated in the accompanying drawings and detailed in the following description. The features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar features and structures throughout the several views of the drawings.

Volar Distal Radius Plate System

Referring now to the drawing, FIGS. 1A-1J depict embodiments of a volar distal radius stabilization system 100 including a bone plate 110 configured to sit against the volar side of the radial bone and one or more bone fasteners 130 configured to be received in the bone plate 110 and secured to the radius 102. The radius 102 or radial bone is one of the two large bones of the forearm, the other being the ulna. The radius 102 extends from the lateral side of the elbow to the thumb side of the wrist and runs parallel to the ulna, which exceeds it in length and size. Near the wrist, the distal end 104 of the radius 102 is large and of quadrilateral form. Although generally described with reference to the radius 102, it will be appreciated that the stabilization systems described herein may be used or adapted to be used for the fixation of other long bones as well, such as the humerus, femur, tibia, etc.

The bone plate 110 extends from a first end 112 configured to be positioned proximate to a shaft portion of radius 102 to a second end 114 configured to be positioned proximate to the distal end 104 of the radius 102. The plate 110 includes a top surface 116 and an opposite, bottom surface 118 configured to contact adjacent bone. The top and bottom surfaces 116, 118 are connected by opposite side surfaces extending from the first to second ends 112, 114 of the plate 110. The bottom surface 118 of the plate 110 includes an anatomic contour configured to follow the best approximation of average distal radial anatomy, flaring up slightly along the radial column and more significantly along the intermediate column of the plate 110. The plate 110 is designed to sit low and have a generally low profile proximal portion. The thickness of the plate 110 may generally be about 2 mm along the shaft and distal intermediate column, tapering to a thickness of 2.5 mm along the distal radial column which allows for the severe angle of the radial styloid fastener. The watershed line of the volar distal radius defines the border between the radiocarpal (RC) joint and the volar surface of the radius 102. A chamfer at the second end 114 on the distal radius column of the plate 110 may help to ensure minimal tendon disruption, for example of the flexor pollicus longus and flexor carpi radialis, by maintaining a lower profile over the tendon sites.

The bone plate 110 includes an elongated portion 140 extending along a longitudinal axis L, having a length greater than its width. The elongated portion 140 is configured to contact the shaft of the radius 102. The elongated portion 140 may terminate at the first end 112 with a taper such that it has a width and/or thickness less than the remainder of the elongated portion 140. A transition region 144 may connect the elongated portion 140 to an enlarged head portion 142. The transition region 144 may extend along an axis T which is generally angled relative to the axis L of the elongated portion 140. The transition region 144 may extend at an angle X relative to the elongated portion

140. The angle X of the transition region 144 relative to the elongated portion 140 may range from about 10-60°, about 20-50°, about 30-40°, about 40-50°, or another appropriate angle. The transition region 144 may generally form a curve from the elongated portion 140 to an end of the enlarged head portion 142.

The transition region 144 may connect to an end portion of the enlarged head portion 142 and the other end portion of the enlarged head portion 142 may be a free end. In other words, the opposite end portion of the enlarged head portion 142, not connected to the transition region 144, is not connected to any other portion of the plate 110. The free end of the enlarged head portion 142 may be separated a distance from the transition region 144 and the elongated portion 140 of the plate 110.

Figure 1C:
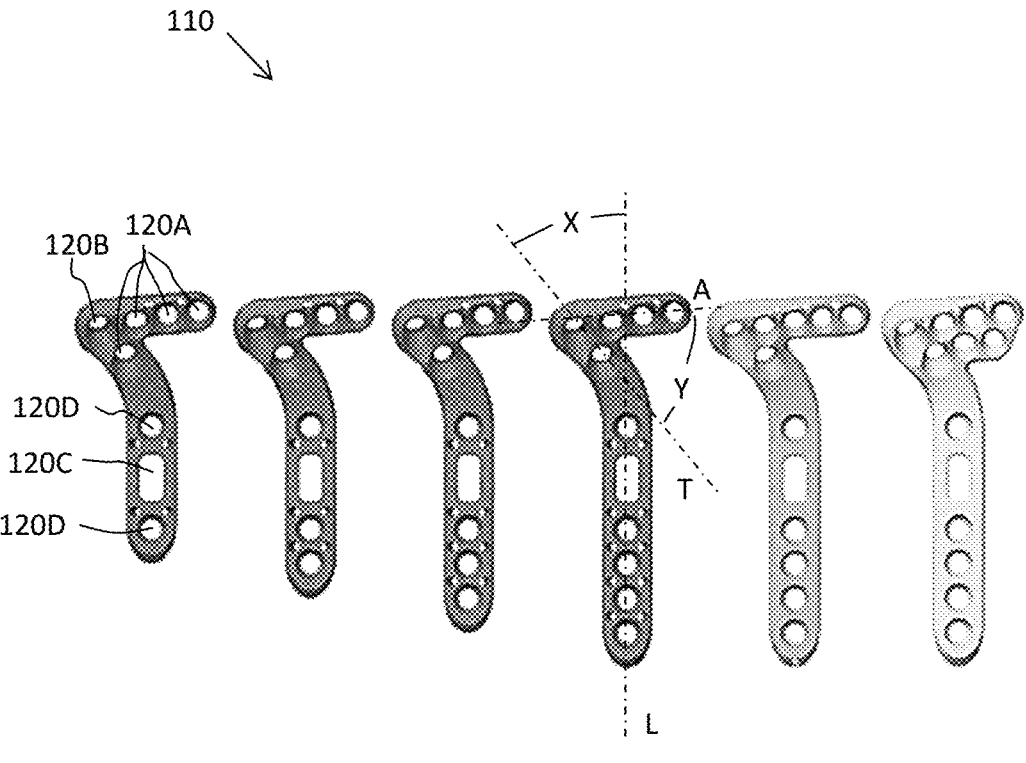

The enlarged head portion 142 or a portion thereof is configured to contact the distal end 104 of the radius 102. The enlarged head portion 142 has a width greater than the width of the elongated portion 140. The enlarged head portion 142 extends along an axis A at an angle Y relative to the transition region 144. The angle Y of the head portion 142 relative to the transition region 144 may range from about 10-60°, about 20-50°, about 30-40°, about 40-50°, or another appropriate angle. Accordingly, the axis A of the enlarged head portion 142 may be transverse to the axis L of the elongated portion 140. In some embodiments, the axis A of the enlarged head portion 142 may be generally perpendicular to the axis L of the elongated portion 140. As best seen in FIG. 1C, the bone plates 110 may be available in a variety of lengths and sizes based on the anatomy of the patient. The plates 110 are configured to sit against the volar side of the radial bone 102. The plates 110 are configured in both left and right designs, in a mirrored configuration, in order to address the anatomy of both the left and right arms of the patient.

Figures 1D, 1E:
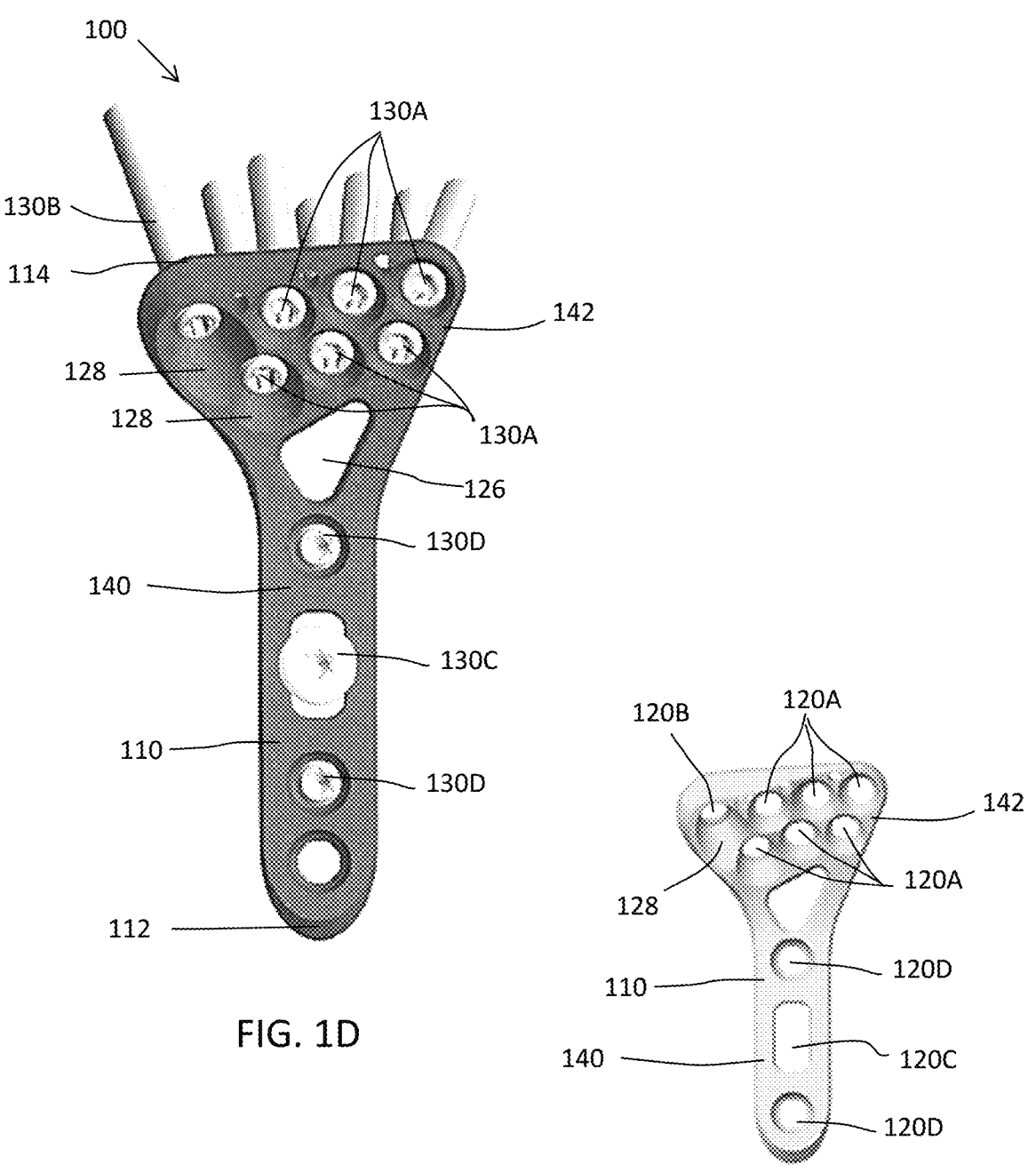
Figures 1F, 1G, 1H, 1I, 1J:
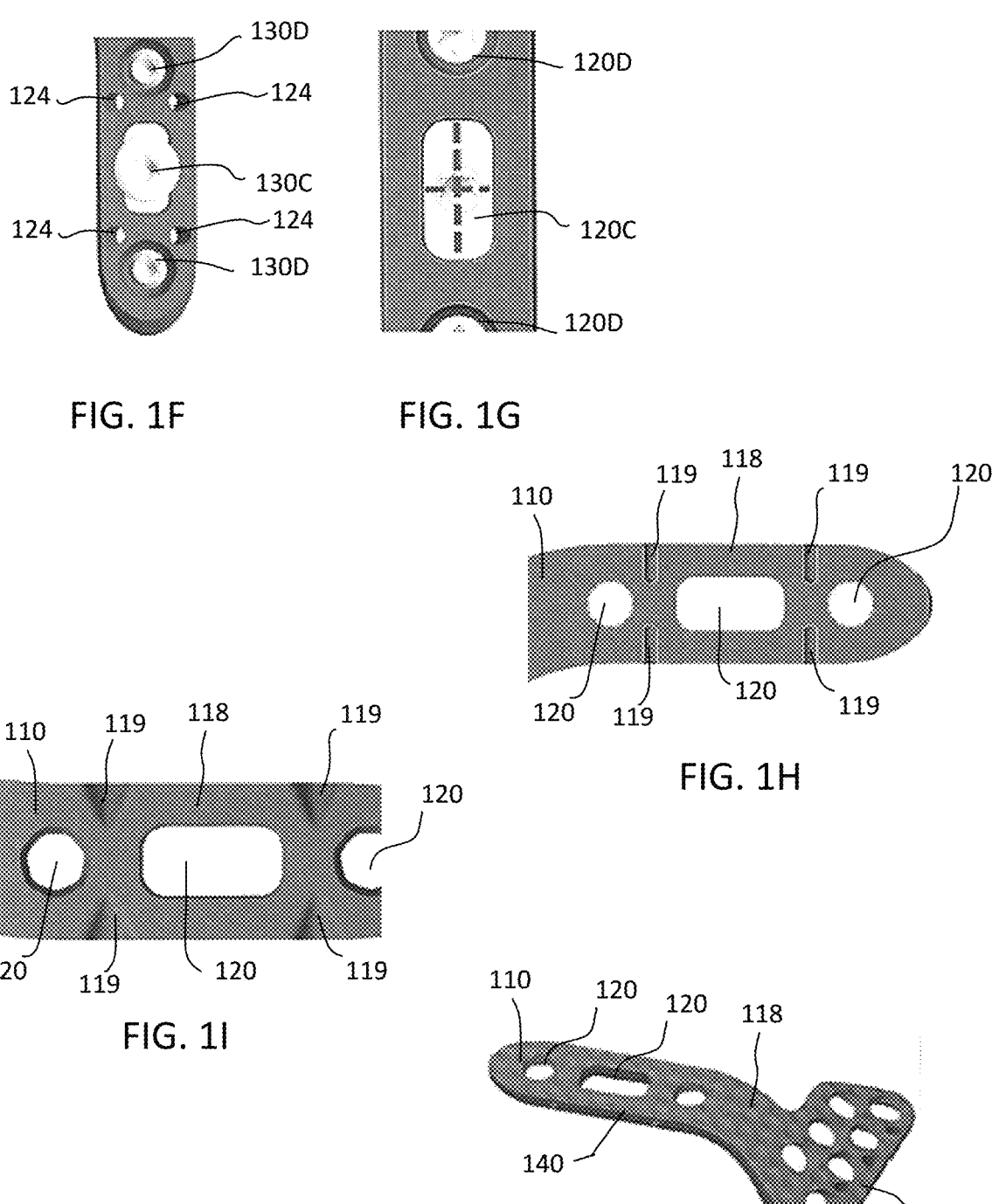

As best seen in FIGS. 1H and 1I, the bottom surface 118 of the plate 110 may include a plurality of recesses 119 located along the elongated portion 140 between the fastener openings 120. In the embodiment shown in FIG. 1H, the recesses 119 are in the form small partial bores in the lateral surface, which are configured to facilitate bending of the plate 110. The recesses 119 remove material such that the plate 110 shield stress from the fastener openings 120, discouraging hole warping effect during recontouring of the plate 110. The recesses 119 may also provide attachment points for plate placement instrumentation (not shown). In the embodiment shown in FIG. 1I, the recesses 119 are in the form of scallop cuts having partially cylindrical valleys cut around a periphery of the bottom surface 118 of the plate 110. This again shields stress from the fastener openings 120 during bending, discouraging hole warping effects while recontouring the plate 110. This also reduces contact between the plate 110 and the bone surface, thereby helping to preserve blood supply to the bone and prevent osteonecrosis. In addition to or in place of the recesses 119, a plurality of dimples, best seen in FIG. 1J, may be positioned along the bottom surface 118 of the plate 110 (e.g., along the entire bottom surface 118 or a portion thereof) to further reduce contact between the plate 110 and bone surface, further helping to preserve blood supply and prevent osteonecrosis.

The plate 110 includes one or more through openings 120 configured to receive one or more bone fasteners 130. The openings 120 extend through the body of the plate 110 from the top surface 116 to the bottom surface 118. The openings 120 may include cylindrical openings, conical openings, elongated openings, threaded openings, textured openings, non-threaded and/or non-textured openings, and the like. The openings 120 may allow for locking of the fastener 130 to the plate 110 or may allow for movement and dynamic compression of the bone. The plate 110 may comprise any suitable number of openings 120 in any suitable configuration. These openings 120 allow surgeons more flexibility for fastener placement, based on preference, anatomy, and fracture location. Surgeons may have differing opinions as to the number, location, and types of fasteners 130. Further, complexity of fracture location and shape makes having as many locations for fasteners 130 as possible necessary. This design offers surgeons a versatile method to achieve higher accuracy in placement of the fasteners 130.

The openings 120 may be configured to receive one or more bone fasteners 130. The fasteners 130 may include locking fasteners, non-locking fasteners, or any other fasteners known in the art. The fasteners 130 may comprise bone screws or the like. The fasteners 130 may also include other fasteners or anchors configured to be secured or engaged with bone, such as nails, spikes, staples, pegs, barbs, hooks, or the like. The fasteners 130 may include fixed and/or variable angle bone screws. The fastener 130 may include a head portion 132 and a shaft portion 134 configured to engage bone. For a locking fastener 130, the shaft portion 134 may be threaded such that the fastener 130 may be threaded into the bone. The head portion 132 may include a textured area, such as threads, around its outer surface sized and configured to engage with the opening 120, for example, and corresponding threads in the opening 120 in order to lock the fastener 130 to the plate 110. In the alternative, for a non-locking fastener 130, the head portion 132 may be substantially smooth to allow for dynamic compression of the bone.

In one embodiment, the enlarged head portion 142 of the plate 110 includes a plurality of holes 120A are aligned so that their nominal trajectories follow the articular surfaces of both the radio-carpal joint and the distal radio ulnar-joint. This allows the fasteners 130A to buttress and support the articular surfaces during fracture reconstruction. As shown in the embodiment in FIGS. 1A-1C, the plate 110 may have a single row of holes 120A generally in alignment and a secondary hole 120A positioned on the transition region 144. FIG. 1C depicts one embodiment of the plate 110 (right most plate 110) having a first, distal row of holes 120A generally in alignment and a second row of holes 120A generally in alignment. The second row of holes 120A may receive fasteners 130A with trajectories converging with the distal row screw trajectories. In an alternative version of the stabilization system 100, shown in FIGS. 1D and 1E, the elongated portion 140 directly transitions into the enlarged head portion 142 and the enlarged head portion 142 is increased in dimension in order to receive the second row of the fasteners 130A.

The holes 120A may be fixed openings configured to accept fixed angle fasteners 130A that can be secured into the distal end 104 of the radius 102. The screw holes 120A and screw heads 132 may have mating conical threads that lock the screw 130A in both angular and axial alignment to prevent collapse and backout. The fasteners 130A may have predetermined trajectories based on the orientations of the openings 120A. An upper portion of the holes 120A may be tapered 128 to allow for the proper positioning of each of the fasteners 130A. Each of the fasteners 130A may be angled along a different trajectory than the other respective fasteners 130A. Some of the fasteners 130A may have a greater angulation than other respective fasteners 130A.

The enlarged head portion of the plate 110 further include a hole 120B configured to receive fastener 130B with a trajectory having the severe angle necessary to reach the tip of the radial styloid. An upper portion of the hole 120B may be tapered 128 and a portion of the plate 110 around the hole 120B may be enlarged or increased in thickness to allow for the proper angle of the fasteners 130B to be achieved. The fastener 130B may be in the form of a polyaxial bone screw, which may be generally larger (e.g., in length and/or diameter) than the other fasteners 130 securing the plate 110 to the bone. The fasteners 130A, 130B are optionally cannulated to allow for precise placement with a k-wire (not shown) if desired by the surgeon. In some embodiments, the fasteners 130A, 130B may include polyaxial screws having self-forming threads that work by displacement of the plate material, which are described in more detail herein.

The plate 110 also include one or more holes 120C present along the elongated portion 140 of the plate 110 and configured to accommodate a compression fastener 130C. As best seen in FIG. 1G, the holes 120C may offer a sliding slot for proximal-distal adjustment of the plate 110 during provisional placement. The slot 120C may allow for proximal adjustment, distal adjustment, and/or medial-lateral adjustment of the plate 110. This allows surgeons to optimally center the plate position along the bone prior to locking screw insertion. The hole or holes 120C may be elongated along the longitudinal axis L of the elongated portion 140 as well as elongated, relative to the fastener 130C, from lateral side to lateral side. The elongated hole or holes 120C may have varying lengths and/or widths. Preferably, the length is greater than the width of the slot 120C.

The hole 120C may be configured to accommodate non-locking, compression screws 130C, the heads of which have a spherical underside, so the screw 130C may be placed at varying angles. The compression screw 130C can be inserted and preliminarily tightened to secure the plate 110 to the bone. As the screw 130C is inserted eccentrically in to the hole 120C, the screw 130C slides down the slot 120C, displacing the plate 110 and the bone as well. The compression screw 130C may have a shorter length and/or a smaller diameter than the screws 130A and/or 130B. If the plate 110 needs to be adjusted later, the screw 130C can be loosened and the plate 110 can be shifted in the proximal, distal, and/or medial-lateral directions. This slot 120C also accommodates reduction of the radius 102 by inserting a longer compression screw 130C and pulling the bone to the plate 110.

The plate 110 may include one or more holes 120D present along the elongated portion 140 of the plate 110 configured to secure the plate 110 to the shaft of the radius 102. The holes 120D may be configured to accommodate fixed and/or variable angle fasteners 130D. For locking fasteners 130D, the screw holes 120D and screw heads 132 may have mating conical threads that lock the screw 130D in both angular and axial alignment to prevent collapse and backout. An upper portion of the holes 120D may be tapered 128, for example, around the perimeter of the hole 120D, to allow for the proper positioning of each of the fasteners 130D. For non-locking fasteners 130D, the head portion 132 may be substantially smooth to allow for dynamic compression of the bone.

The plate 110 including head portion 142 and/or the elongated portion 140 may further comprise a plurality of openings 124 configured to receive one or more k-wires (not shown). The k-wire holes 124 may comprise small diameter holes (e.g., having a diameter significantly smaller than the fastener openings 120). The k-wire holes 124 may allow preliminary placement of the plate 110 against the bone and/or to aid in reduction of the fracture. The distal k-wire holes 124 on the head portion 142 may ensure a trajectory to follow the RC joint and provide direction during insertion of the distal locking screws. The proximal k-wire holes in the elongated portion 140 of the plate 110 are arrange between fastener openings 120 and may be angled relative to the surface of the plate 110 to avoid intrusion into areas where instrumentation must pass during screw insertion.

In the embodiment shown in FIGS. 1D and 1E, the plate 110 may also comprise a window 126. The window 126 may provide visualization of the plate 110 with respect to the radius 102 in the operating environment and on imaging (e.g., fluoroscopy). The window 126 is show as generally an asymmetrical triangle, but it envisioned that the window 126, if present, may be of any suitable shape, size, and dimension.

The bone plate 110 may be attached to a proximal humerus to fixate one or more bone fractures or fragments and thereby promote healing of the bone. In one embodiment, the plate 110 further restores the anatomic alignment of the radius 102. The plate 110 may be positioned against the volar side of the radial bone. One or more k-wires may be supplied through the k-wire holes 124 to assist with preliminary placement of the plate 110. Pilot holes may be drilled through the fastener openings 120 to prepare to receive the respective fasteners 130. The fasteners 130A, 130B, 130C, 130D may be positioned through the respective openings 120A, 120B, 120C, 120D and into the radius 102. The fasteners 130 may be affixed to the bone in any suitable order, number, and orientation depending on the anatomy of the bone and the fracture.

Alternative Hole Configurations

The fixed and variable angle, locking and non-locking openings 120, 220 (e.g., including openings 120A, 120B, 120C, 120D) and respective fasteners 130, 230 (e.g., including 130A, 130B, 130C, 130D) described herein may be substituted with or include one or more of the following openings 20 and/or fasteners 30, 40. The openings 20 and/or fasteners 30, 40 are generally described with reference to a generic plate 10, which may include plate 110, 210, 310, 410, 510, 610, or any other suitable plate design.

Referring now to the drawing, FIGS. 2-18 depict alternative openings 20 in plate 10. The openings 20 extending through the plate 10 are configured to accept locking fasteners 30, non-locking fasteners 40, or a combination of both locking and non-locking fasteners 30, 40 that are able to dynamically compress the bone and/or affix the plate 10 to the bone. When plating diaphyseal bone, surgeons may use a combination of both locking and non-locking fasteners 30, 40 that are able to dynamically compress bone and to connect the bone and the plate 10. Dynamic compression may also be desirable to create interfragmental compression while tightening the fasteners 30, 40.

Figure 2:
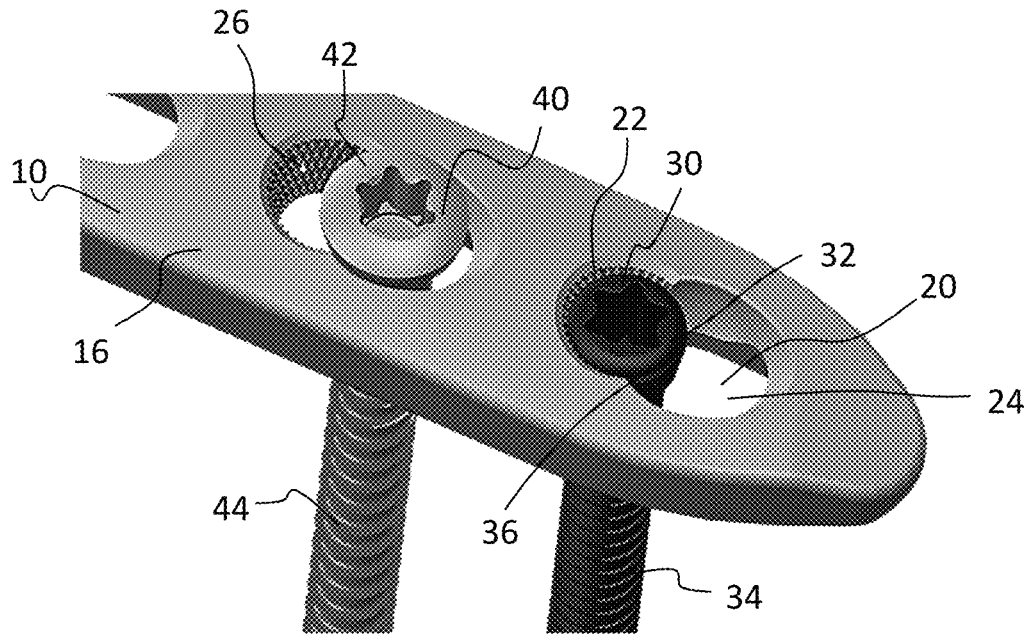
FIG. 2 is a top perspective view of two fasteners engaged with combination holes according to an embodiment.

The plate 10 includes a top surface 16 and an opposite, bottom surface 18 configured to contact adjacent bone. The plate 10 includes one or more through openings 20 configured to receive one or more bone fasteners 30, 40. The openings 20 extend through the body of the plate 10 from the top surface 16 to the bottom surface 18. In the embodiments depicted in FIGS. 2-3, for example, the openings 20 may be in the form of a combination opening that has at least two overlapping holes. As shown in FIG. 2, the combination opening 20 includes a first hole 22 overlapping a second hole 24. One of the holes 22 may be configured to be the locking hole 22, thereby able to receive and secure the locking fastener 30 to the plate 10, and the other of the holes 24 may be configured to be the dynamic compression hole 24, thereby allowing the non-locking fastener 40 to freely move in the hole 24 and apply dynamic compression. The locking hole 22 may have one or more locking features designed to engage with a locking fastener 30, and the dynamic compression hole 24 may be elongated, for example, along the central longitudinal axis of the plate 10. The screw holes 22, 24 are not constrained to parallel axes. This hole geometry may be used in bone plates 10 to utilize either fixed angle or variable angle locking screws 30 and/or polyaxial non-locking screws 40 that can achieve dynamic compression.

These openings 20 allow surgeons more flexibility for fastener placement, based on preference, anatomy, and fracture location. Surgeons may have differing opinions as to whether non-locking or locking screws 30, 40 (or some combination of the two) should be used in diaphyseal bone. Further, complexity of fracture location and shape makes having as many locations for fasteners 30, 40 as possible necessary. This design offers surgeons a versatile method to achieve higher accuracy in placement of locking and/or non-locking screws 30, 40.

As best seen in FIG. 2, the locking and non-locking fasteners 30, 40 are shown. The locking and non-locking fasteners 30, 40 may include traditional fasteners known in the art. The locking and non-locking fasteners 30, 40 may comprise bone screws or the like. The fasteners 30, 40 may also include other fasteners or anchors configured to be secured or engaged with bone, such as nails, spikes, staples, pegs, barbs, hooks, or the like. The fasteners 30, 40 may include fixed and/or variable angle bone screws.

The locking fastener 30 may include a head portion 32 and a shaft portion 34 configured to engage bone. The shaft portion 34 may be threaded such that the fastener 30 may be threaded into the bone. The head portion 32 of the locking fastener 30 includes a textured area 36 around its outer surface sized and configured to engage with the locking hole 22 of the combination opening 20. The textured area 36 may include threads, ridges, bumps, dimples, serrations, or other types of textured areas. As shown, the texture area 36 preferably includes a threaded portion extending substantially from the top of the head portion 32 to the bottom of the head portion 32 proximate to the shaft portion 34. Thus, when the textured area 36 engages the locking hole 22, the locking fastener 30 is thereby locked to the plate 10.

The non-locking fastener 40 includes a head portion 42 and a shaft portion 44 configured to engage bone. The shaft portion 44 may be threaded such that the fastener 40 may be threaded into the bone. The head portion 42 of the non-locking fastener 40 is substantially smooth around its outer surface such that is able to slide along the elongated compression hole 24. Thus, the non-locking fastener 30 may be coupled to the plate 10, but not locked thereto to enable dynamic compression of the bone. It will be recognized that the head portions 32, 42 of the fasteners 30, 40 may include a recess configured to receive a driver or the like.

The locking hole portion 22 of the combination opening 20 includes a textured portion 26. The textured portion 26 may include threads, ridges, bumps, dimples, serrations, knurls, or other types of textured areas. The textured portion 26 may be of the same type (e.g., mating surfaces) or different from the textured area 36 of the locking fastener 30. As shown, the textured portion 26 is serrated or knurled along an inner portion of the hole 22. The knurled surface may include straight, angled, or crossed lines cut or rolled into the material. In the embodiment shown in FIG. 2, the textured portion 26 extends along substantially the entire inner surface of the hole 22. With reference to the embodiment shown in FIG. 3, the combination hole 20 is substantially the same as that shown in FIG. 2 except that the textured portion 26 the locking hole 22 now includes a thin centralized textured ribbon of material. For example, the textured portion 26 takes up about half or less of the surface area of the hole 22. In this instance, only a portion of the textured area 36 of the head portion 32 of the locking fastener 30 engages with and locks to the textured portion 26 of the hole 22.

Figure 3:
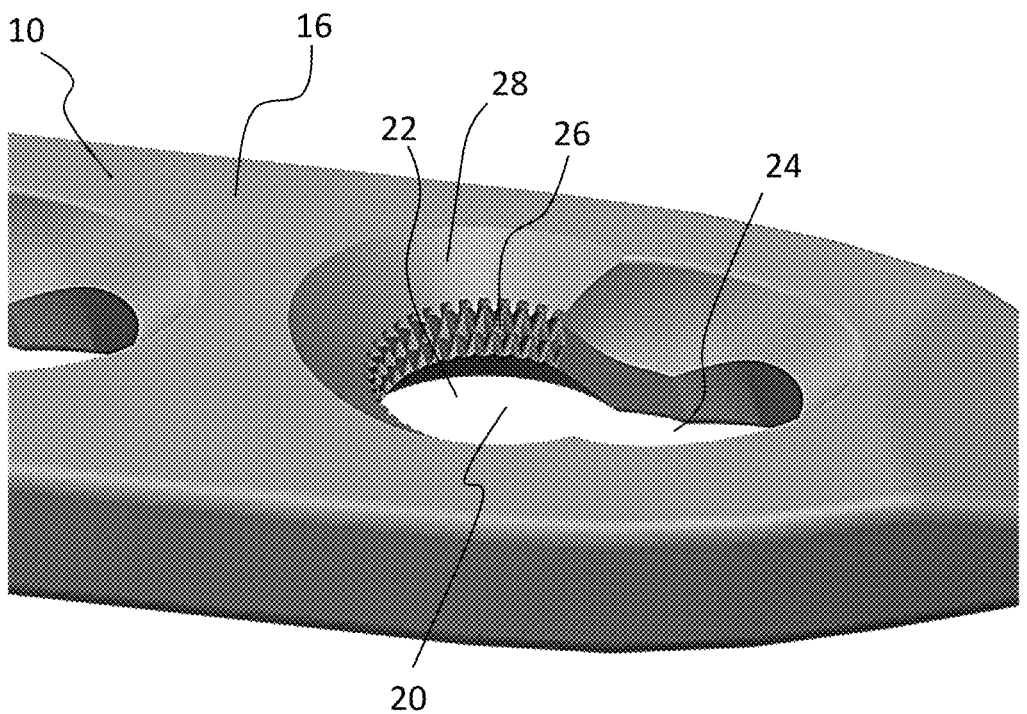
FIG. 3 is a close-up view of an alternative version of a combination hole according to another embodiment.

An upper portion of the hole 22 may be tapered 28, without texturing, for example, to facilitate alignment of the fastener 30 with the opening 20. As shown in FIG. 3, this tapered portion 28 is enlarged in area relative to the embodiment in FIG. 2. The hole 22 may be configured to receive a fixed or variable angle fastener 30. The hole 22 may be generally conical in shape such that it is wider near the top surface 16 of the plate 10 and narrower toward the bottom surface 18 of the plate 10. The tapered portion 28 and/or the textured area 26 may be conical in shape. In this embodiment, the locking hole 22 is a textured fixed angle conical hole configured to receive locking fastener 30. The textured holes 22 may deform as the fastener head 32 interferes with the textured portion 26 of the hole 22, thereby providing a positive lock between the fastener 30 and the plate 10.

The second hole portion 24 of the combination opening 20 may be an elongated dynamic compression hole. The dynamic compression hole 24 may be elongated such that it has a length greater than its width. The hole 24 may be elongated along the longitudinal axis of the plate 10. In the alternative, the hole 24 may be generally cylindrical such that the hole 24 only permits polyaxial movement of the fastener 40. The inner surface of the hole 24 may be substantially smooth such that the non-locking fastener 40 is able to freely pivot and/or slide along the hole 24. This provides for at least two directions of compressive force (e.g., along the longitudinal axis and perpendicular to the longitudinal axis of the plate 10). The head portion 42 of the non-locking fastener 40 may be substantially smooth around its outer surface. The head portion 42 is sized and configured to engage with and be retained within the hole portion 24 of the combination opening 20. The hole 24 may be configured to receive a fixed or variable angle fastener 40. In one embodiment, the hole 24 may be generally conical in shape and/or tapered such that it is wider near the top surface 16 of the plate 10 and narrower toward the bottom surface 18 of the plate 10. In this embodiment, the hole 24 is a smooth variable angle conical hole configured to receive the non-locking fastener 40. The hole 24 may receive the fastener head 42 allowing movement of the fastener 40, for example, in a polyaxial fashion and/or along the length of the hole 22, thereby providing dynamic compression of the bone.

Turning now to FIGS. 4-7, alternative types of openings 20A-20G, which provide for locking and/or non-locking, dynamic compression are provided. As many of the features of these openings are similar to the combination openings 20 described already for FIGS. 2-3, only the different features will be further explained.

Figure 4A:
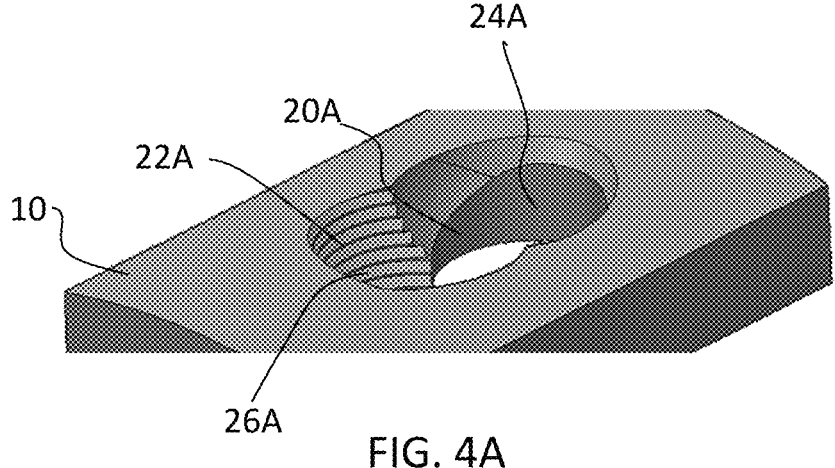
FIGS. 4A-4C show a perspective view, top view, and cross-section view, respectively, of an another embodiment of a combination hole.
Figure 4B:
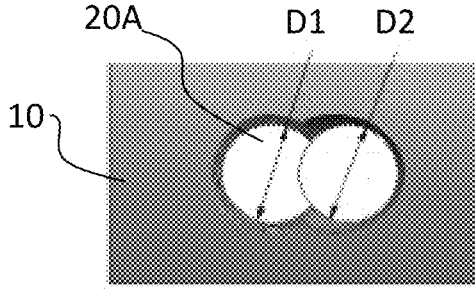
Figure 4C:
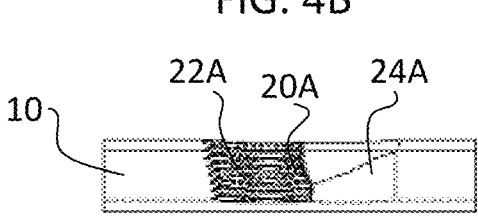

With reference to FIGS. 4A-4C, the combination opening 20A is similar to combination opening 20 except that the dynamic compression hole 24A has the same general diameter as the locking hole 22A, and the locking hole 22A includes a different type of textured portion 26A. In this embodiment, the locking hole 22A has a first diameter D1, and the dynamic compression hole 24A has a second diameter D2. Unlike the elongated hole 24 described earlier, dynamic compression hole 24A has substantially same diameter as the locking hole 22A. Thus, the first and second diameters D1, D2 are substantially the same. The hole 24A may be formed by milling or drilling a sphere out of the plate 10 in the center of the circle with tapers or ramps on either side. The hole 24A is not elongated, but is generally circular and the non-locking fastener 40 will be allowed to translate in the hole 24A because the diameter of the head portion 42 and/or shaft (e.g., bone thread) will be smaller than the size of the hole 24A in the plate 10. With respect to hole 22A, the textured portion 26A of the hole 22A may be in the form of a tapered thread. This tapered thread may generally correspond to a similar tapered thread on the locking fastener 30. This hole 22A also does not include a tapered portion, and the textured portion 26A begins at the intersection with the top surface 16 of the plate 10. This alternative opening 20A also provides for the use of both locking and non-locking fasteners 30, 40 that are able to dynamically compress bone and/or lock the plate 10 to the bone.

Turning now to FIGS. 5A-5C, the combination opening 20B is similar to other combination openings except that the locking hole 22B includes a different type of textured portion 26B. The textured portion 26B includes a series of alternating recesses and protrusions around a central portion of the hole 22B. The recesses may be in form of a wave of alternating cutouts extending around the inner perimeter of the hole 22B. The textured portion 26B may lock the fastener 30 with a friction fit or may be modified during insertion of the fastener 30 to form a lock in situ. In this embodiment, the locking hole may allow for polyaxial locking. The plate 10 and the locking fastener 30 may be made of dissimilar materials having dissimilar hardness values. For example, the fastener 30 may have a higher hardness (e.g., on the Rockwell scale) relative to the plate 10, which may be formed of a material having a lower relative hardness value. Due to the increased hardness, the head portion 32 of the locking fastener 30 may create a thread in the plate 10 as the fastener 30 is inserted (e.g., threaded) into the hole 22B, thereby locking the fastener 30 to the plate 10.

Figure 6A:
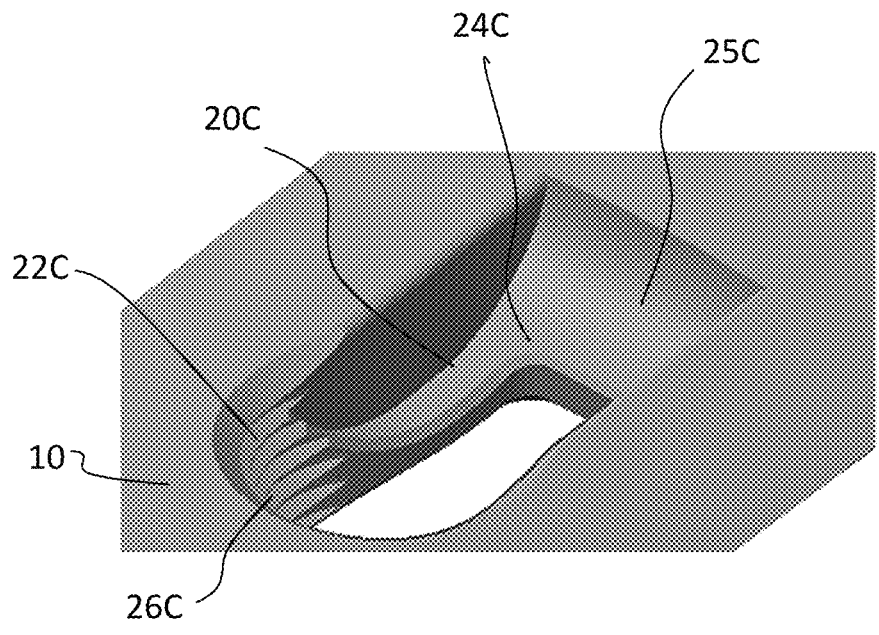
FIGS. 6A-6C show a perspective view, top view, and cross-section view, respectively, of an another embodiment of a hole for receiving a fastener.
Figure 6B:
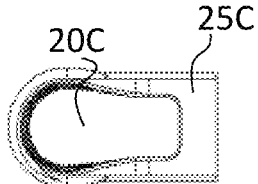
Figure 6C:
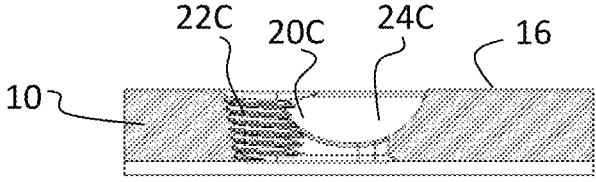

With reference to FIGS. 6A-6C, the opening 20C includes locking hole 22C and dynamic compression hole 24C with a more open configuration. The locking portion 22C has a textured portion 26C in the form of a tapered thread. This tapered thread may generally correspond to a similar tapered thread on the locking fastener 30. The opposite portion 24C of the opening 20C is oblong with a ramp 25C milled into the top surface 16 of the plate 10 to allow for dynamic compression. As best seen in FIG. 6C, the ramp may be partially spherical in shape and extend from the top surface 16 of the plate 10 and connect to the textured portion 26C. When viewed from above in FIG. 6B, the ramp 25C creates a square-like, key-hole, and/or non-hole geometry that sweeps into the tapered threaded locking hole 22C. This alternative opening 20C also provides for the use of both locking and non-locking fasteners 30, 40 that are able to dynamically compress bone and/or lock the plate 10 to the bone.

Figure 7A:
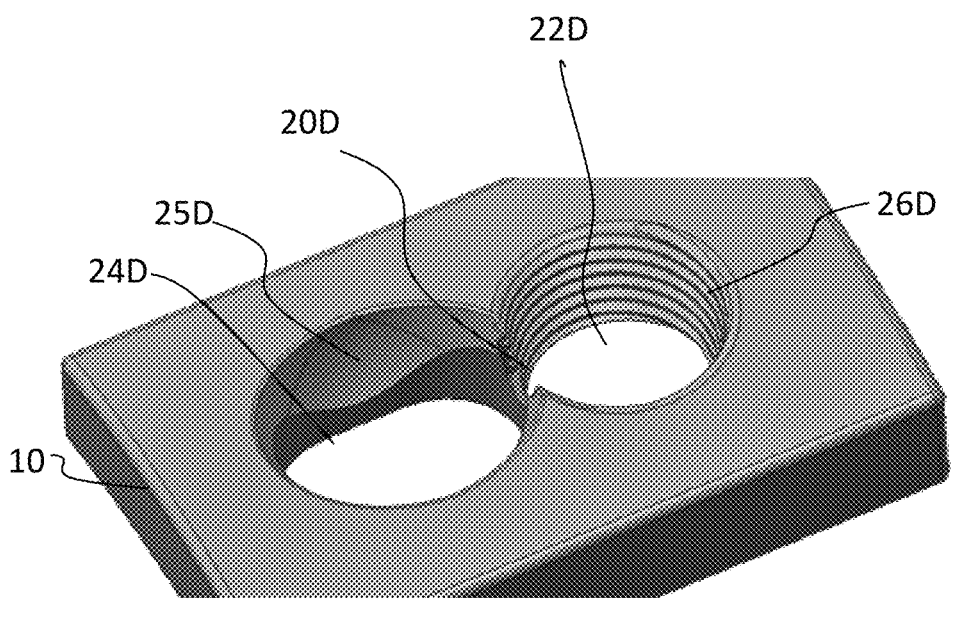
FIGS. 7A-7C show a perspective view, top view, and cross-section view, respectively, of an another embodiment of a combination hole.
Figure 7B:
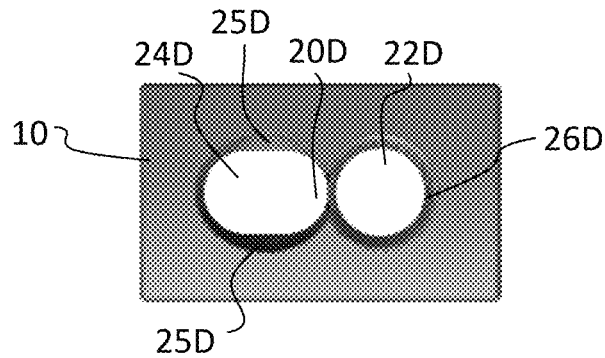
Figure 7C:
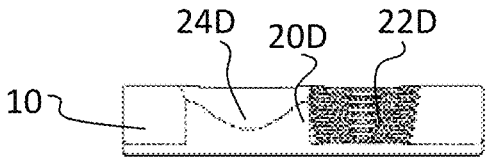

Turning now to FIGS. 7A-7C, the opening 20D includes locking hole 22D and dynamic compression hole 24D. These holes 22D, 24D are connected and close together but are not overlapping. The holes 22D, 24D are separated by a small portion or sliver of plate material proximate to the lower portion of the holes 22D, 24D (e.g., at bottom surface 18 of the plate 10 and partially extending between the holes 22D, 24D). The locking portion 22D has a textured portion 26D in the form of a tapered thread. The textured portion 26D extends around almost the entire circumference of the hole 22D except where connected to hole 24D. The dynamic compression hole 24D is elongated and has ramped portions 25D on opposite sides of the hole 24D to receive fastener 40. This configuration allows for a very close population of holes 22D, 24D on the plate 10 while giving structural stability at the holes 22D, 24D.

Figure 8A:
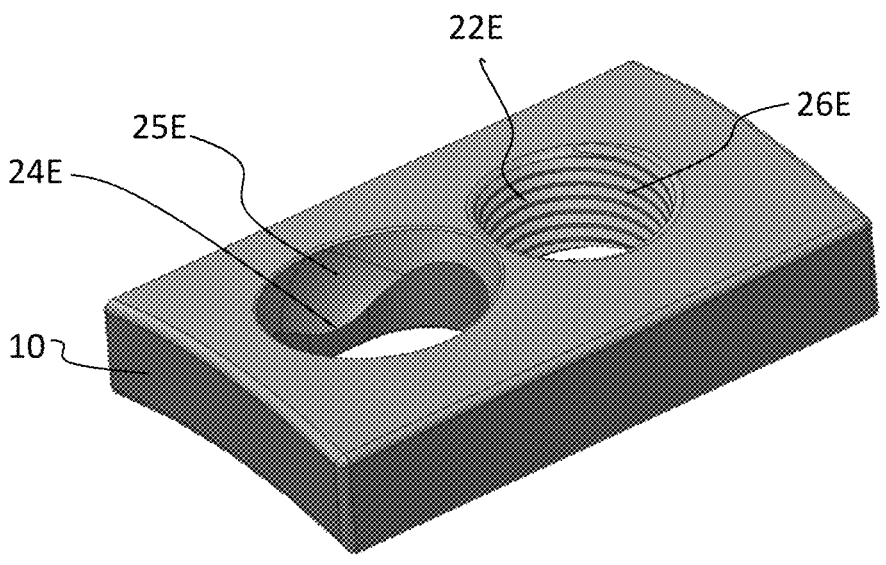
FIGS. 8A-8C show a perspective view, top view, and cross-section view, respectively, of an another embodiment of separate locking and non-locking holes.
Figure 8B:
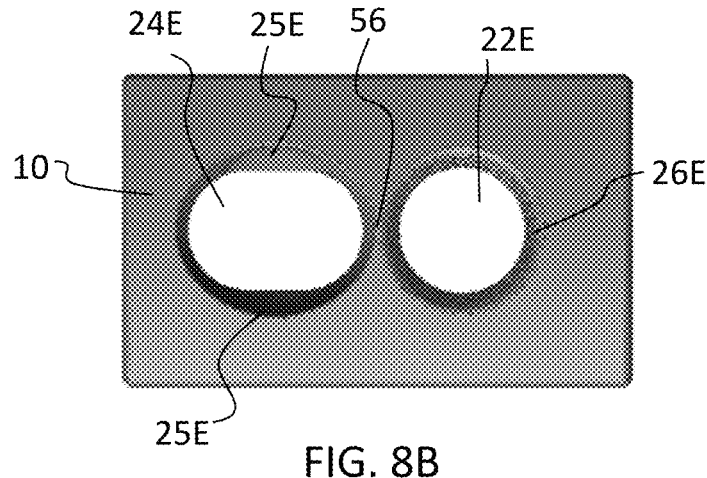
Figure 8C:
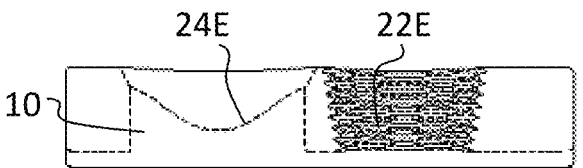

With reference to FIGS. 8A-8C, locking hole 22E and dynamic compression hole 24E are adjacent, but separate from one another. The holes 22E, 24E are completely separated from one another by a wall 56 of plate material. The locking portion 22E has a textured portion 26E in the form of a tapered thread extends around the entire perimeter of the hole 22E. The dynamic compression hole 24E is elongated and has ramped portions 25E on opposite sides of the hole 24E. This configuration also allows for a very close population of holes 22E, 24E on the plate 10 while giving options for both locking and/or dynamic compression.

Turning now to FIGS. 9A-9D, an alternative version of opening 20F is provided. In this embodiment, the hole construct 20F is comprised of at least three overlapping conical threaded holes in the plate 10. The opening 20F includes a first, locking hole 22F, a second hole 24F, and a third hole 23F arranged along a longitudinal axis of the plate 10. The third hole 23F is the mirror image of hole 24F across the first locking hole 22F. The conically threaded holes 22F, 23F, 24F may or may not have parallel axes. Each hole 22F, 23F, 24F may include a textured portion 26F, for example, in the form of one or more threaded portions. Thus, the locking fastener 30 may lock to any of the holes 22F, 23F, 24F. Although each of the holes 22F, 23F, 24F are shown in with the textured portion 26F, it will be appreciated that one or more of the holes 22F, 23F, 24F may have a substantially smooth inner portion instead of the textured portion 26F. The upper part of the hole construct at the first and second ends of the hole 20F each have a ramped feature 25F (e.g., adjacent to holes 23F and 24F) to allow for dynamic compression of the plate 10. In addition, the ramped feature 25F may span the three or more conical holes 22F, 23F, 24F (e.g., around the entire perimeter of the opening 20F).

Figure 9A:
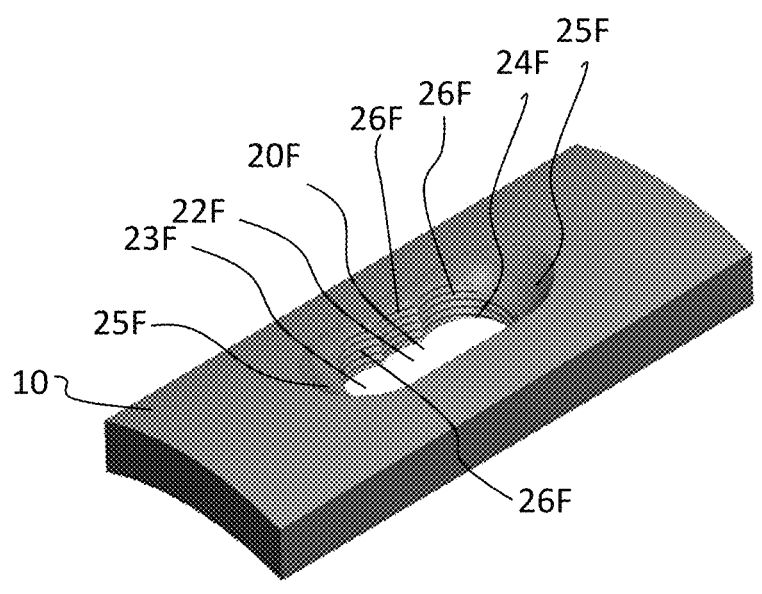
FIGS. 9A-9D show a perspective view, a top view, a cross-section view, and a perspective view with a locking fastener, respectively, according to another embodiment of a plate including three overlapping locking and non-locking holes.
Figure 9B:
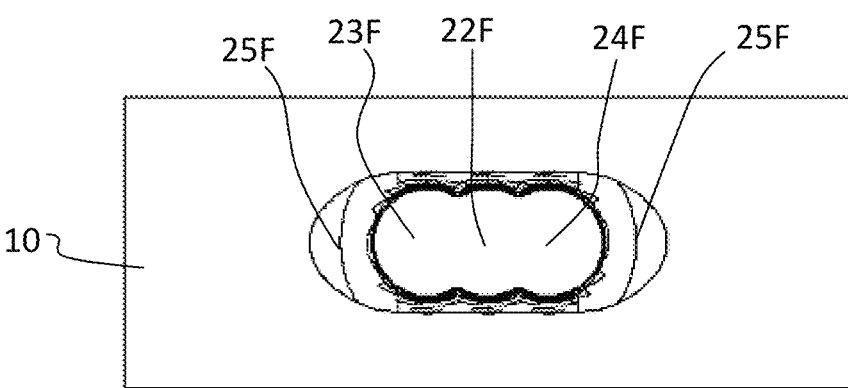
Figure 9C:
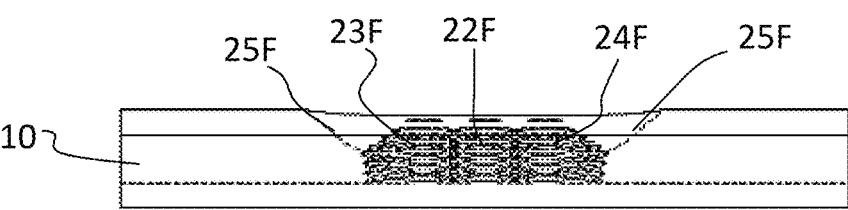
Figure 9D:
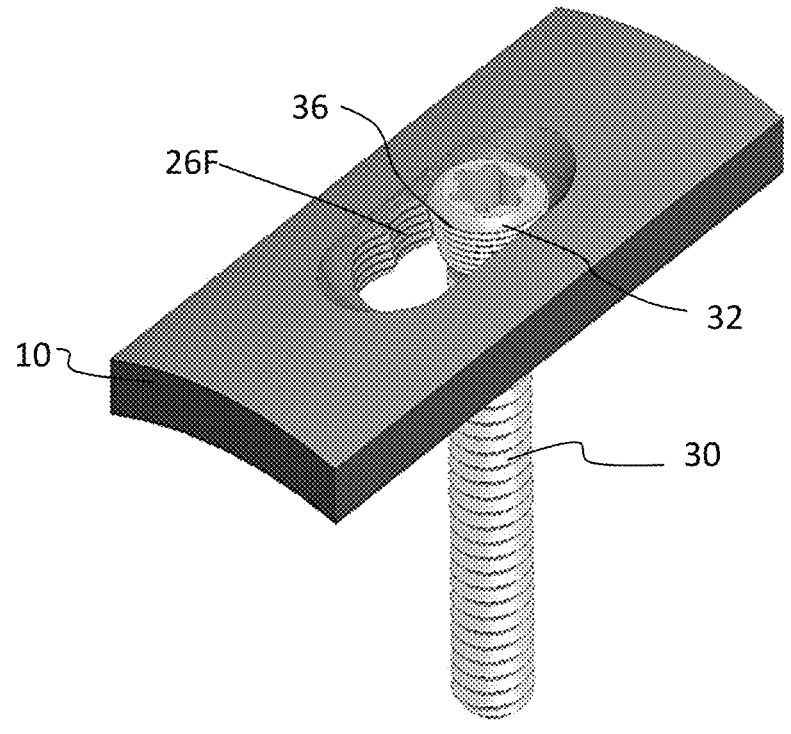

The non-locking compression fasteners 40 may have a major bone thread diameter such that the fastener 40 can translate between overlapping holes 22F, 24F, 23F without interference. As best seen in FIG. 9D, the locking fastener 30 may include a textured area 36, for example, in the form of a thread, configured to engage with the textured portion 26F of any of the holes 22F, 23F, 24F. The hole geometry of opening 20F can be applied to bone plates 10 to utilize either fixed angle and/or variable angle locking screws 30 and/or polyaxial non-locking screws 40 that can achieve dynamic compression. This allows surgeons more flexibility for screw placement, based on preference, anatomy, and fracture location.

Figure 10A:
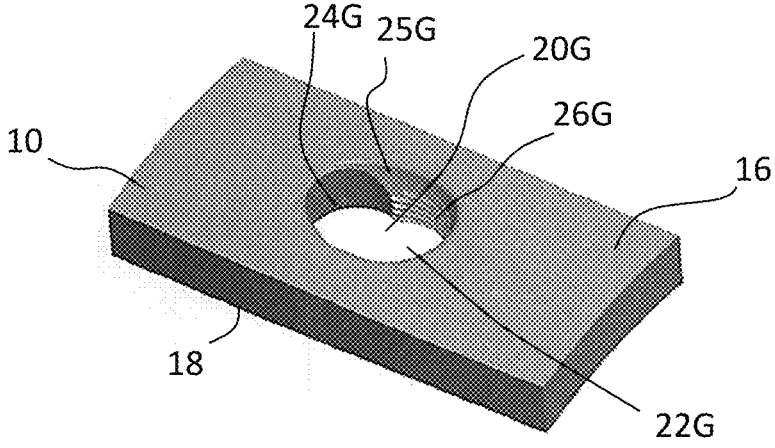
FIGS. 10A-10B show perspective views of a plate according to another embodiment with locking and non-locking functionality.
Figure 10B:
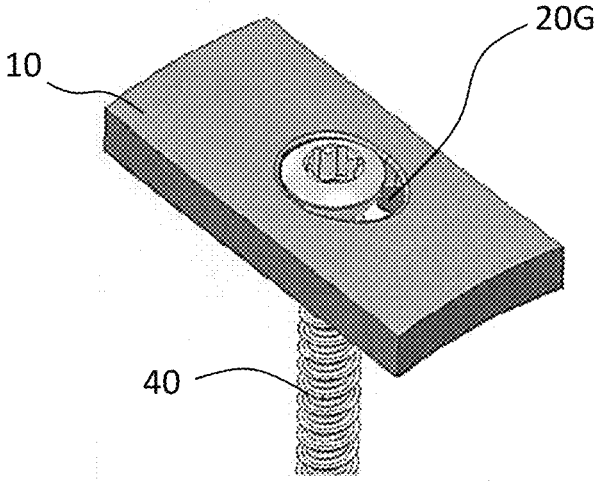

Turning now to FIGS. 10A-10B, another embodiment of opening 20G is provided. This opening 20G may be comprised of one elongate hole or slot extending from the top surface 16 to the bottom surface 18 of the plate 10. A locking portion 22G of the opening 20G may include a textured portion 26G having straight machine threads. The threads may extend more than 180 degrees to retain the locking fastener 30. A non-locking portion 24G of the opening 20G may be positioned opposite the locking portion 22G to complete the opening 20G. The upper part of the opening 20G may have one or more ramped features 25G to allow for dynamic compression of the plate 10. The ramp 25G may span along the entire upper perimeter of the elongated slot 20G or a portion thereof. The compression screws 40 may have a major bone thread diameter such that the screws 40 are able to translate along the opening 20G without interference.

With reference to FIGS. 11A-11E, alternative embodiments of the locking fastener 30 may be used with any plate 10. The head portion 32 of the fastener 30 may include a textured area 36 in the form of a thread, for example, to lock the fastener 30 to the plate 10. The fastener 30 and/or plate 10 may also include one or more mechanisms to prevent back out of the fastener 30 from the plate 10. In FIG. 11A, the head portion 32 includes at threaded portion 36A (e.g., having straight threads) that interface with the plate 10 and the top of the head extends larger than the threads. The head portion 32 bottoms out when the fastener 30 is fully inserted and creates preload in the fastener 30, thus locking the fastener 30 rotationally. In FIG. 11B, the head portion 32 includes threaded portion 36B. The head portion 32 has a constant major diameter while the minor diameter is tapered. The thread depth may go to zero at the top of the head portion 32 of the screw 30. The first few turns smoothly insert, but as the tapered portion of the male thread engages with the plate 10, interference occurs, jamming and/or locking the screw 30 and preventing backout. In FIG. 11C, a screw thread 36C on the head portion 32, similar to the design in FIG. 11B, except the minor diameter of the screw 30 stays constant while the major diameter of the head portion 32 gets larger toward the top of the screw 30. A similar jamming and locking mechanism results through tightening of the screw 30 in the plate 10. In FIG. 11D, the threaded portion 36D has areas of varying pitch. In particular, a straight screw thread on the head portion 32 of the screw 30 has a similar pitch to that of the plate 10 at the bottom of the head portion 32 of the screw 30. The pitch then increases or decreases towards the top of the head portion 32, which thereby results in jamming of the threads and preventing unwanted backout of the screw 30. In an alternative variation of the concept of FIG. 11D, shown in FIG. 11E, the opening in the plate 10 is provided with areas of varying pitch while the pitch of the threaded portion 36D remains constant. For example, the head portion 32 may include a straight thread with a constant pitch. The upper surface of the plate 10 may include a thread pitch is similar to that of the screw 30, but towards the bottom surface of the plate 10, the thread pitch would either increase or decrease to lock the screw 30 to the plate 10.

Figure 12A:
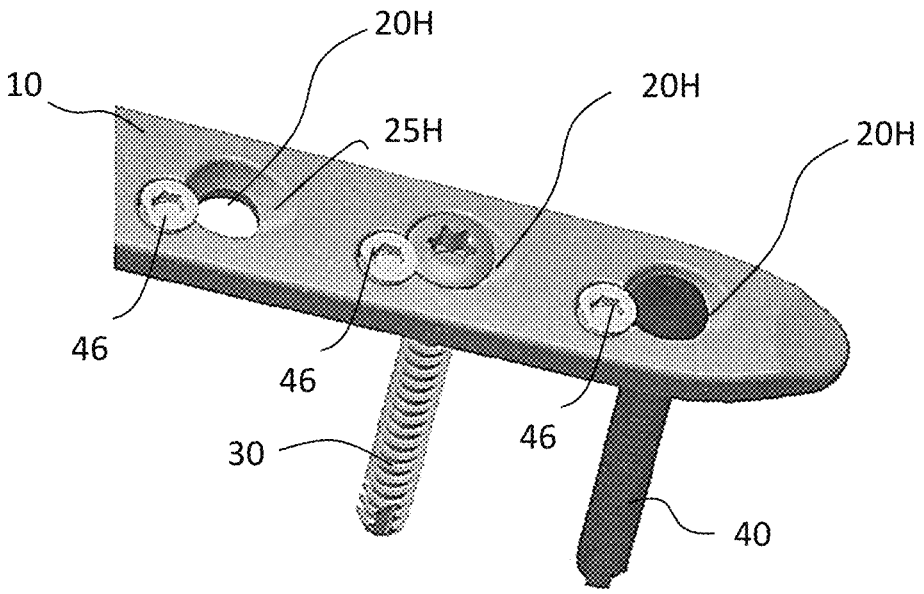
FIGS. 12A and 12B depict a perspective view and cross-section view of an alternative version of a plate with blocking screws.
Figure 12B:
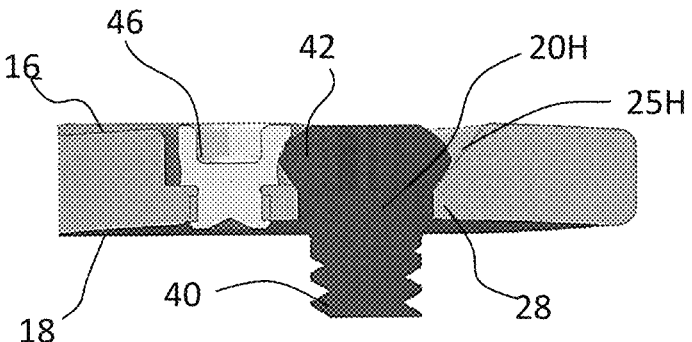

Turning now to FIGS. 12A and 12B, the plate 10 includes an additional anti-backout feature. In this embodiment, the plate 10 includes cylindrical holes or openings 20H configured to accept either the compression fastener 40 or the locking fastener 30. Each opening 20H may include a ramped portion 25H extending around a portion or the entire perimeter of the opening 20H to allow for dynamic compression with a compression fastener 40. Each opening 20H may include a cylindrical feature to provide angular stability with a locking fastener 30. The opening 20H may also include an angular taper 28 to cause compressive tightening between the locking fastener 30 and the cylindrical opening 20H. Each opening 20H has an accompanying blocking screw 46 that can be actuated to block the fastener 30, 40 from backing out. The blocking screw 46 may extend from a first end at the top surface 16 to a second end at the bottom surface 18 of the plate 10. The first end of the blocking screw 46 may include a recess sized to receive an instrument to rotate the blocking screw 46 from an unblocked position to a blocked position. The blocked position may include a portion of the blocking screw 46 covering a portion of the head portion 42 of the fastener 40, thereby further preventing backout of the fastener 40 from the plate 10.

According to yet another embodiment, the plate 10 may include one or more openings 20 configured to receive the locking fastener 30 having self-forming threads that work by displacement of the plate material to lock the fastener 30 to the plate 10. Turning now to FIGS. 13-18, the locking fastener 30 and alternative embodiments of the openings 20 in the plate 10 are shown. In these embodiments, the locking mechanism of the fastener 30 (e.g., bone screw) to the internal fixation plate 10 may allow for variable angle screw insertion. The fastener 30 may be inserted within an angular cone where the force required to dislodge the head portion 32 of the fastener 30 is substantially equivalent to the force required when the fastener 30 is inserted perpendicular to the plate 10. The holes or openings 20 in the plate 10 may be shaped such that the fastener 30 may be inserted at different angles. The geometry of the opening 20 is conducive to catching the threads on the head portion 32 of the fastener 30 and to reduce the axial force necessary to initiate the thread formation.

The locking mechanism includes a fastener 30 having a head portion 32 with self-forming threads that displace the plate material. The plate 10 may be made of a material softer than the fastener 30 to facilitate displacement. For example, the plate 10 may be comprised of titanium, alloys, polymers, or other materials having a lower material hardness (e.g., Rockwell hardness). The fastener 30 may be made of a harder relative material, for example, comprised of cobalt chrome, tungsten, alloys, or other materials having a higher material hardness. Preferably, the fastener 30 is comprised of a material having a strong, stiff, and high surface hardness which facilitates the thread forming process. The forming mechanism works by displacement of material rather than removal of the material of the plate 10, thereby minimizing fragments or chips which are created from tapping.

Figure 13A:
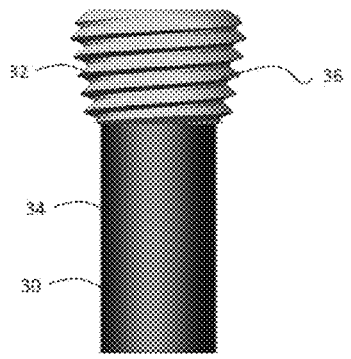
FIGS. 13A and 13B depict a fastener according to another embodiment with self-forming threads configured to form threads in the opening of a plate.
Figure 13B:
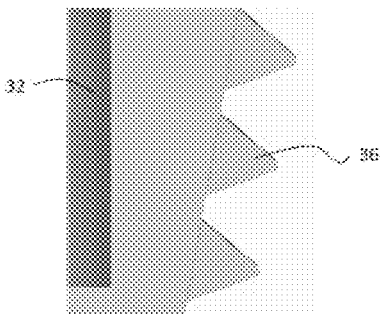
Figure 14A:
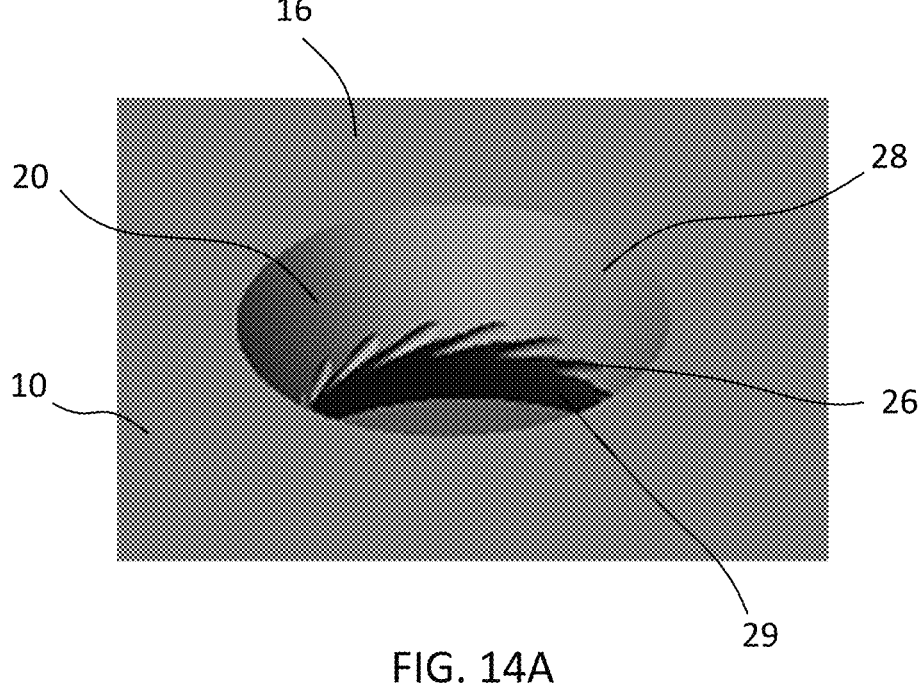
FIGS. 14A and 14B depict an opening in a plate according to one embodiment having a windswept cut configured to receive the self-forming threads of the fastener of FIGS. 13A-13B.
Figure 14B:
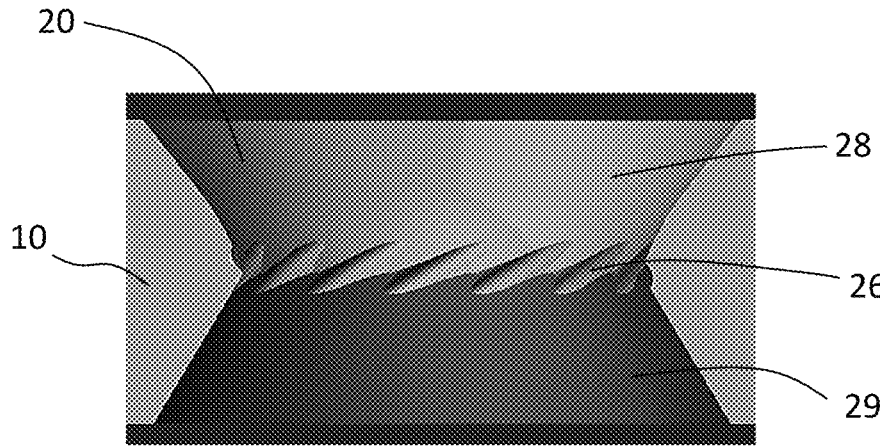

In FIGS. 13A-13B, the locking fastener 30 includes a head portion 32 and a shaft portion 34 configured to engage bone. Although not shown, the shaft portion 34 may be threaded such that the fastener 30 may be threaded into the bone. The head portion 32 may be tapered (e.g., at an angle of about) 20° such that the fit within the opening 20 in the plate 10 becomes tighter as the fastener 30 is advanced in to the bone. The head portion 32 of the locking fastener 30 includes a textured area 36 around its outer surface sized and configured to engage an opening 20 in the plate 10. The textured area 36 may include threads, ridges, bumps, dimples, serrations, or other types of textured areas. As shown, the textured area 36 preferably includes a threaded portion extending substantially from the top of the head portion 32 to the bottom of the head portion 32 proximate to the shaft portion 34. The threads 36 may run generally perpendicular to the conical surface of the head portion 32. The threaded portion 36 is in the form of self-forming threads configured to displace the plate material and create threads in the opening 20 of the plate 10. The threaded portion has an exaggerated sharp thread peak to facilitate cutting or forming of the plate material.

Turning now to FIGS. 14-17, alternative versions of the openings 20 are shown before being tapped with the fastener 30. Once the fastener 30 is inserted, these openings 20 are modified based on the self-forming threads. The geometry of the openings 20 are conducive to catching the threads 36 and designed to reduce the axial force necessary to initiate the thread formation. An upper portion of the hole 20 may be tapered 28, for example, with a conical straight tapered surface cut through the top surface 16 of the plate 10 for clearance of the head portion 32 of the fastener 30 during off angle insertion. A lower portion of hole 20 may further be tapered 29, for example, with a conical straight tapered surface cut through the bottom surface 18 of the plate 10 for clearance of the shaft portion 34 during off angle insertion. The upper tapered portion 28 may be larger, for example, with a larger degree of taper than the lower tapered portion 29. For example, the upper tapered portion 28 may have a taper in a range from about 60-90°, 70-80°, or 72-78°, preferably about 70°, 75°, or 80° whereas the lower tapered portion 29 may have a taper in a range from about 50-70°, 55-65°, or 57-63°, preferably about 55°, 60°, or 65°. The upper and/or lowered tapered portions 28, 29 may be substantially conical (e.g., FIGS. 14B, 15B, 16B) or may be segmented with more than one section, such as two separate conical sections having different diameters or degrees of taper (e.g., FIGS. 17A and 17B).

At the intersection between the upper tapered portion 28 and the lower tapered portion 29 a narrowed central portion may have a textured portion 26. As described herein, the textured portion 26 may include threads, ridges, bumps, dimples, serrations, or other types of textured areas. In the embodiment shown in FIGS. 14A-14B, the textured portion 26 includes a windswept cut design comprised of a plurality of shallow cuts where each cut overlaps the next. For example, the windswept design may include a plurality of threadlike helical cut sweeps. Each cut has a smooth transition into the inner diameter of the hole 20 (e.g., into the upper and lower tapered portions 28, 29). The windswept cuts provide a positive surface for the self-forming threads to cut into, thereby helping to prevent peeling of the newly formed threads into the plate 10.

Figure 15A:
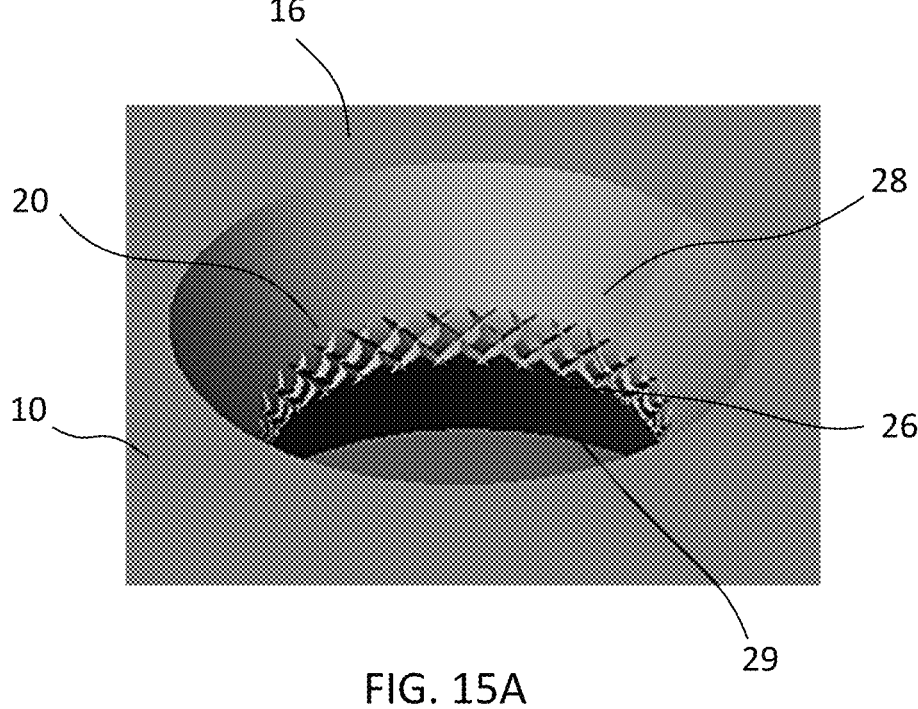
FIGS. 15A and 15B depict an opening in a plate according to another embodiment having a knurled cut configured to receive the self-forming threads of the fastener of FIGS. 13A-13B.
Figure 15B:
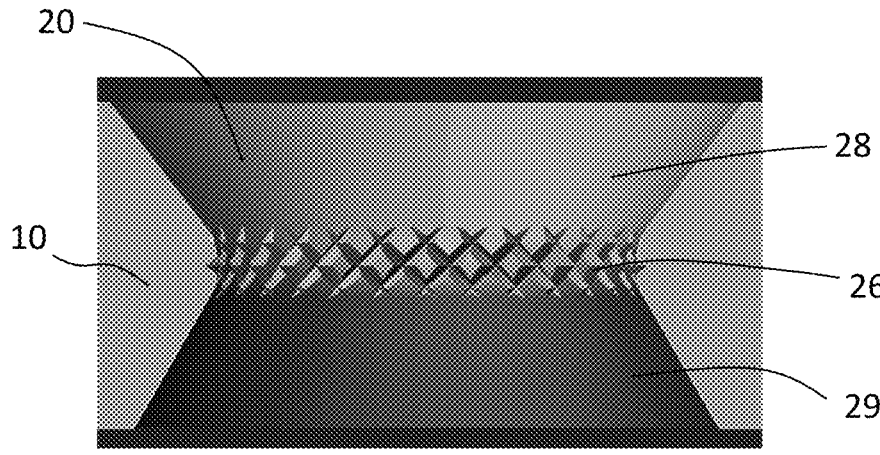
Figure 16A:
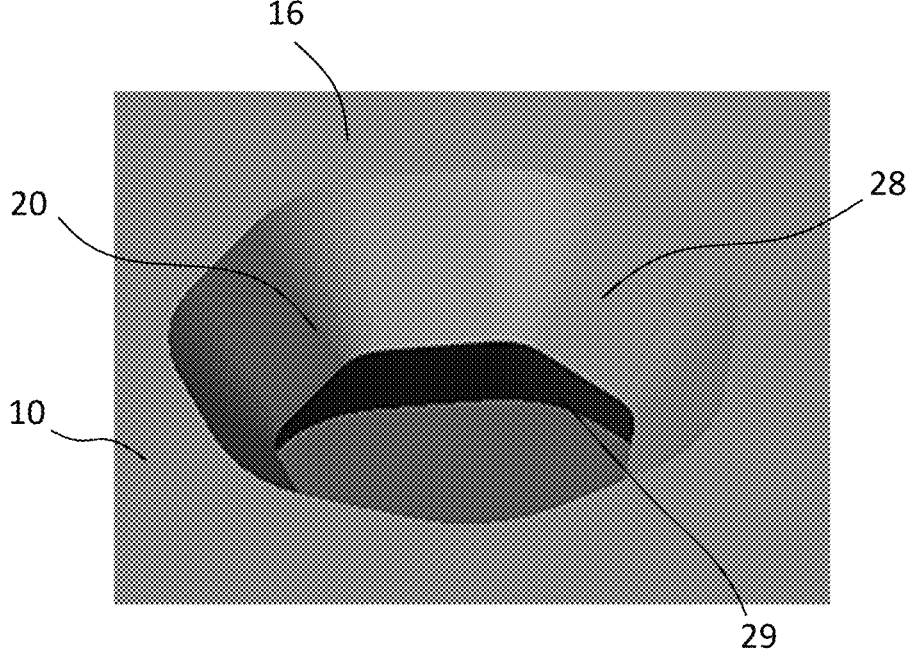
FIGS. 16A and 16B depict an opening in a plate according to another embodiment having a polygonal cut configured to receive the self-forming threads of the fastener of FIGS. 13A-13B.
Figure 16B:
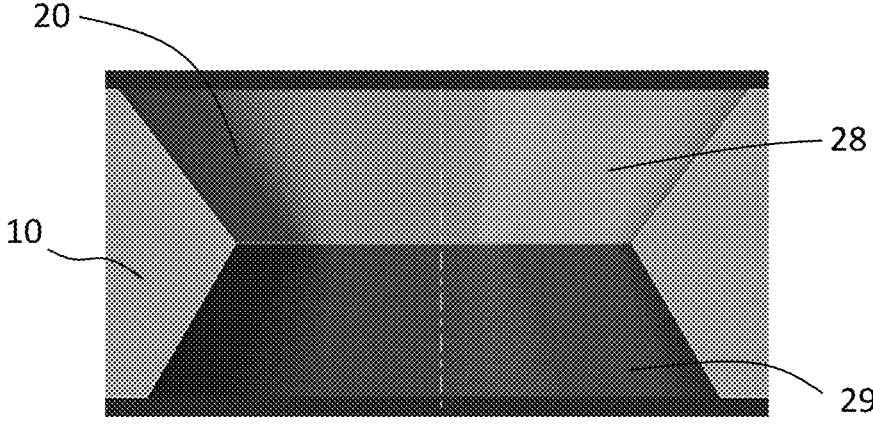

In FIGS. 15A-15B, the textured portion 26 includes a knurled cut design. A rounded transition between the upper tapered portion 28 and the lower tapered portion 29 (e.g., the two conical cuts) provides a workable surface for the knurling process as well as a surface for the head portion 32 to be able to roll over during off-axis locking. The knurled design may include a plurality of shallow knurled grooves set in a diamond pattern (e.g., about) 45° where each cut overlaps the next. The knurled grooves allow for the self-forming threads to cut more deeply into the material and reduce the necessary axial force to begin the thread forming process. FIGS. 16A-16B depict a polygon form cut design. In this design, there is no textured portion at the transition between the upper tapered portion 28 and the lower tapered portion 29. Instead, the narrowed central region has an overall polygonal form such that the hole 20 is neither cylindrical nor conical. The polygonal shape includes a number of sides with distinct linear section of material and rounded corners around which the form cut is allowed to sweep. For example, the polygonal shape may be substantially hexagonal (6-sided), heptagonal (7-sided), octagonal (8-sided), etc. The hole 20 may also be represented without lobe cuts, as a single concentric ring with the same geometry.

Figure 17A:
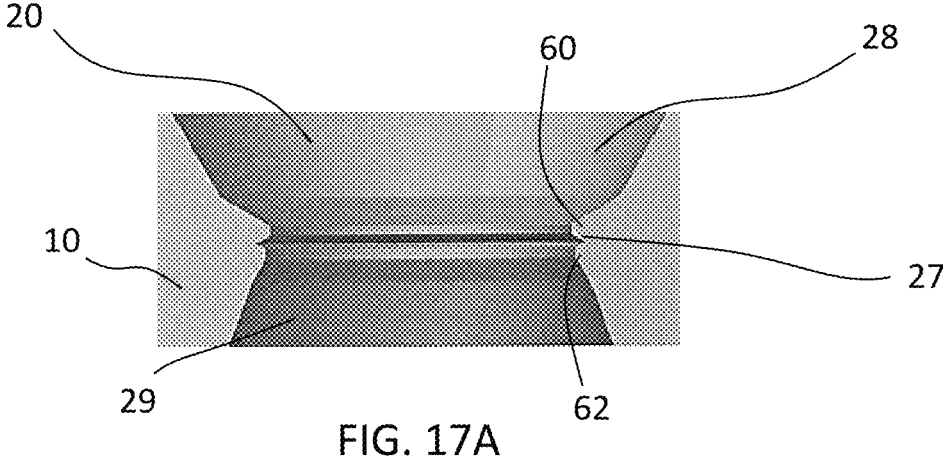
FIG. 17A depicts an alternative opening in a plate according to another embodiment.

In FIG. 17A, the upper tapered portion 28 includes a conical straight tapered surface cut for clearance of the head portion 32 of the fastener 30 during off angle insertion. The upper tapered portion 28 is segmented to have an upper area with a larger area relative to a lower area proximate the transition to the lower tapered portion 29 having a narrower diameter. The central area between the upper and lower tapered portions 28, 29, where the thread forming process occurs, includes two peaks or concentric rings of material (e.g., a superficial ring 60 and a deep ring 62) with a groove 27 being locating in between for material removal and thread forming relief. The groove 27 between the rings 60, 62 may be angled, for example, in the range of about 40-80°, about 50-70°, or about 60°. The superficial ring 60 is of a slightly smaller inner diameter than the deep ring 62, as the superficial ring 60 is responsible for supporting a majority of the cantilever loads. The deep ring 62 provides additional fixation and support during off-angle insertion as well as additional support during nominal trajectory insertion. The lower tapered portion 29 includes a straight tapered surface that provides clearance for the shaft 34 of the fastener 30 when inserted off angle.

Figure 17B:
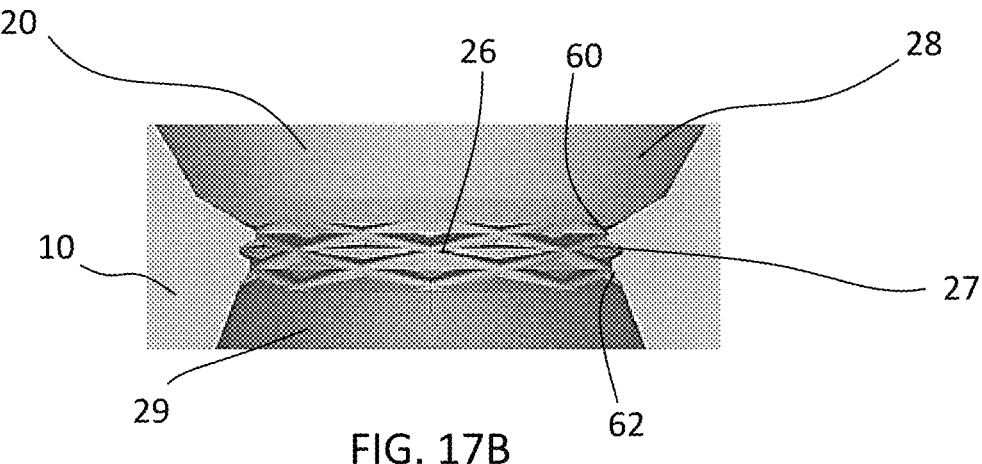
FIG. 17B depicts another alternative opening in a plate according to yet another embodiment.

The embodiment of the opening 20 in FIG. 17B is similar to FIG. 17A, but further includes textured portion 26 in the form of a plurality of helical swept cuts at the transition between the upper tapered portion 28 and the lower tapered portion 29. The shallow helical cuts or windswept cuts may include a series of cuts at a steep pitch. The windswept cuts may be angled, for example, at about 50-70°, or about 60°. The same number of cuts may be made in both a clockwise and counter-clockwise fashion. The cuts may create plateaus of material protruding into the opening 20. The resultant geometry provides positive surfaces for the fastener 30 to cut into, which can dramatically reduce the axial force necessary to lock the fastener 30 to the plate 10. Thus mechanism does not need to rely on bone purchase in order to engage the threads in the head portion 32 of the fastener 30. The material removed during insertion of the fastener 30 allows the self-forming threads to cut deeper by removing material which much be formed and reducing friction between the fastener 30 and the plate 10 during the forming process.

FIGS. 18A-18D depict a screw-plate assembly. The assembly, in FIG. 18C, shows the locking fastener 30 placed at an angle, other than perpendicular, to the upper surface 16 of the plate 10. In FIG. 18D, a non-locking fastener 40 is placed generally perpendicular to the plate 10. It will be appreciated that the locking fastener 30 and non-locking fastener 40 may be oriented at any appropriate angle relative to the plate 10. The section view in FIG. 18C shows the thread engagement with the plate 10 in which material of the plate 10 is displaced around the threads of the fastener 30. By using the self-forming threads, the fastener 30 is able to be inserted into the plate 10 at variable angles and engages with the plate 10 with one-step locking requiring no additional steps to lock the fastener 30 to the plate 10. The section view in FIG. 18D show the compressive, non-locking screw 40 received in the opening 20, without threadedly locking thereto. The non-locking screw 40 may provide for dynamic compression of the bone. Accordingly, the fasteners and openings described herein provide a wide variety of options for the surgeon, thereby providing appropriate locking and/or unlocking capability for dynamic compression depending on the desired treatment of the fracture and the bone.

Dia-Meta Volar Distal Radius Plate System

Figure 19:
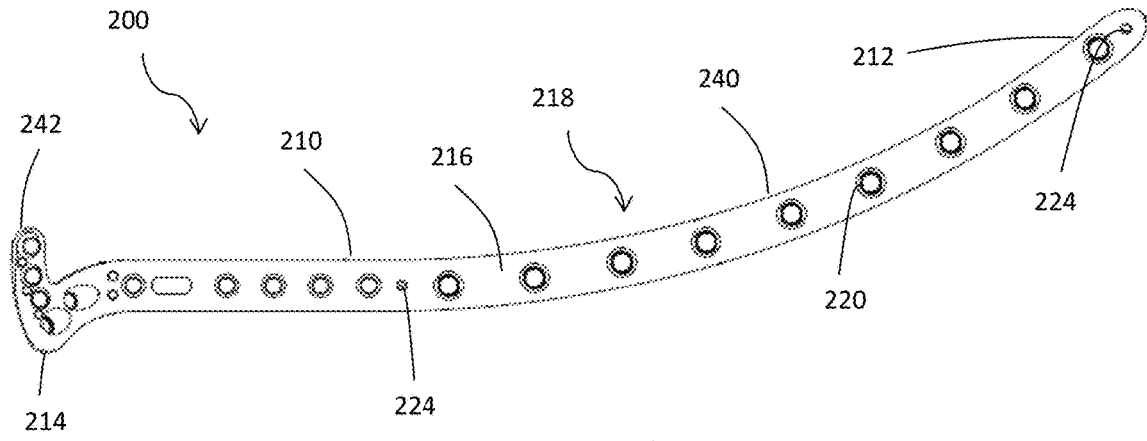
FIG. 19 depicts a stabilization system according to one embodiment including a volar distal radius dia-meta bone plate.

FIG. 19 depicts embodiments of a dia-meta volar distal radius stabilization system 200 including a bone plate 210 configured to sit against the volar side of the radial bone and one or more bone fasteners are configured to be received in the bone plate 210 and secured to the radius and radial shaft of a bone. Although generally described with reference to the radius and radial shaft, it will be appreciated that the stabilization system 200 described herein may be used or adapted to be used for the fixation of other long bones as well, such as the humerus, femur, tibia, etc.

The bone plate 210 extends from a first end 212 configured to be positioned on a shaft portion of radial bone to a second end 214 configured to be positioned proximate to the distal end of the radius. The plate 210 includes a top surface 216 and an opposite, bottom surface 218 configured to contact adjacent bone. The top and bottom surfaces 216, 218 are connected by opposite side surfaces extending from the first to second ends 212, 214 of the plate 210. The bottom surface 218 of the plate 210 includes an anatomic contour configured to follow the best approximation of average distal radial anatomy, flaring up slightly along the radial column and more significantly along the intermediate column of the plate 210. The plate 210 is designed to sit low and have a generally low profile proximal portion. The thickness of the plate 210 may generally be about 2 mm along the shaft and distal intermediate column, tapering to a thickness of 2.5 mm along the distal radial column which allows for the severe angle of the radial styloid fastener. The thickness of the plate 210 may generally increase towards the first end 212 when compared to the second end 214. In addition, the width of the plate 210 proximate the first end 212 and along the elongate portion 240 may be thicker than the width of the plate at the second end 214. The design of plate 210 allows for an easy transition from the second end 214 of the plate 210 to the elongate portion 240 to the first end 212 of the plate 210 to address fractures proximal to the second end of the plate 214 while also providing adequate support in the radial shat of the bone.

The second end 214 of the bone plate 210 toward the elongate portion 240 of the bone plate 210 is very similar to the bone plate 110, thus the features and disclosures set forth above relating to the bone plate 110 are equally applicable to bone plate 210 and are incorporated in their entirety herein.

Looking at the elongate portion or dia-meta portion 240 of the plate 210, the plate 210 includes one or more through openings 220 configured to receive one or more bone fasteners. The openings 220 extend through the body of the plate 210 from the top surface 216 to the bottom surface 218. The openings 220 may include cylindrical openings, conical openings, elongated openings, threaded openings, textured openings, non-threaded and/or non-textured openings, and the like. The openings 220 may allow for locking of the fastener to the plate 210 or may allow for movement and dynamic compression of the bone. The plate 210 may comprise any suitable number of openings 220 in any suitable configuration. These openings 220 allow surgeons more flexibility for fastener placement, based on preference, anatomy, and fracture location. Surgeons may have differing opinions as to the number, location, and types of fasteners. Further, complexity of fracture location and shape makes having as many locations for fasteners as possible necessary. This design offers surgeons a versatile method to achieve higher accuracy in placement of the fasteners.

The openings 220 may be configured to receive one or more bone fasteners. The fasteners may include locking fasteners, non-locking fasteners, or any other fasteners known in the art. The fasteners may comprise bone screws or the like. The fasteners may also include other fasteners or anchors configured to be secured or engaged with bone, such as nails, spikes, staples, pegs, barbs, hooks, or the like. The fasteners may include fixed and/or variable angle bone screws. The fastener may include a head portion and a shaft portion configured to engage bone. For a locking fastener, the shaft portion may be threaded such that the fastener may be threaded into the bone. The head portion may include a textured area, such as threads, around its outer surface sized and configured to engage with the opening 220, for example, and corresponding threads in the opening 220 in order to lock the fastener to the plate 210. In the alternative, for a non-locking fastener, the head portion may be substantially smooth to allow for dynamic compression of the bone.

The plate 210 may further comprise a plurality of openings 224 configured to receive one or more k-wires (not shown). The k-wire holes 224 may comprise small diameter holes (e.g., having a diameter significantly smaller than the fastener openings 220). The k-wire holes 224 may allow preliminary placement of the plate 210 against the bone and/or to aid in reduction of the fracture. The distal k-wire holes 224 on the head portion 242 may ensure a trajectory to follow the RC joint and provide direction during insertion of the distal locking screws. The proximal k-wire holes in the elongated portion 240 of the plate 210 are arrange between fastener openings 220 and may be angled relative to the surface of the plate 210 to avoid intrusion into areas where instrumentation must pass during screw insertion.

Dorsal Plate System

Figure 20:
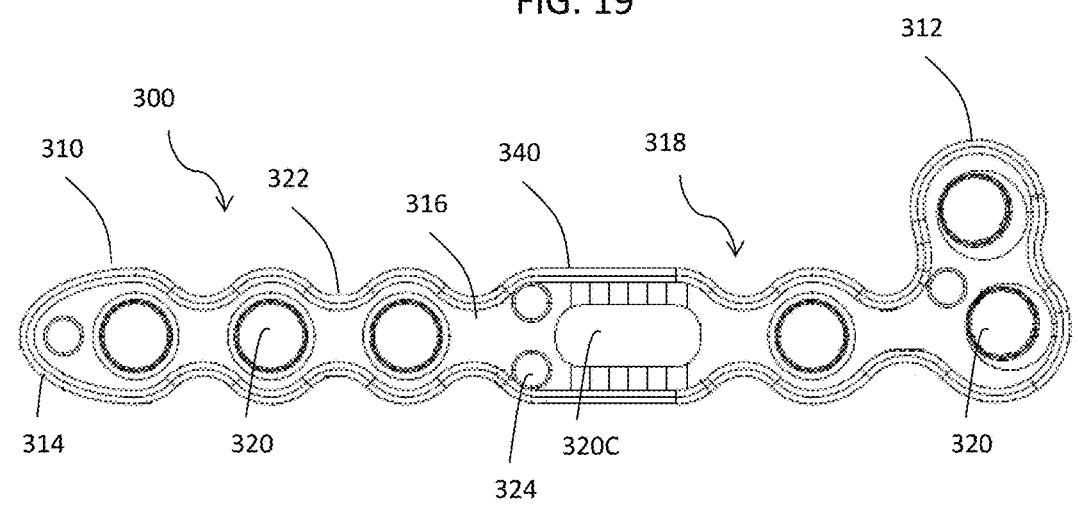
FIG. 20 depicts a stabilization system according to one embodiment including an acute dorsal bone plate.
Figure 21:
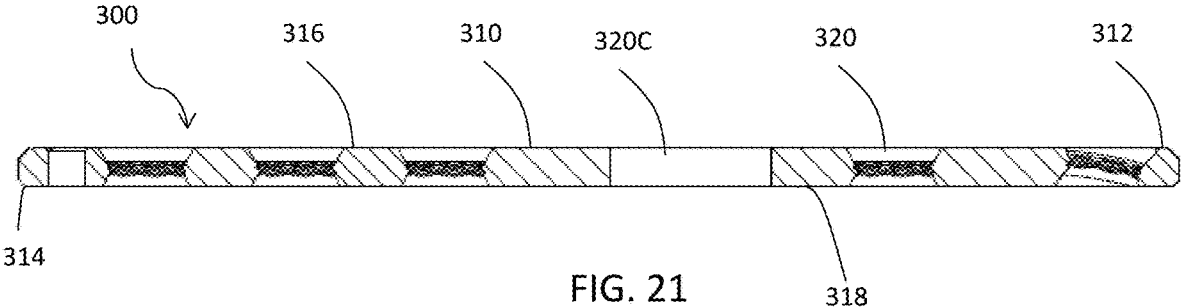
FIG. 21 is a cross sectional view of the dorsal bone plate of FIG. 20.
Figure 22:
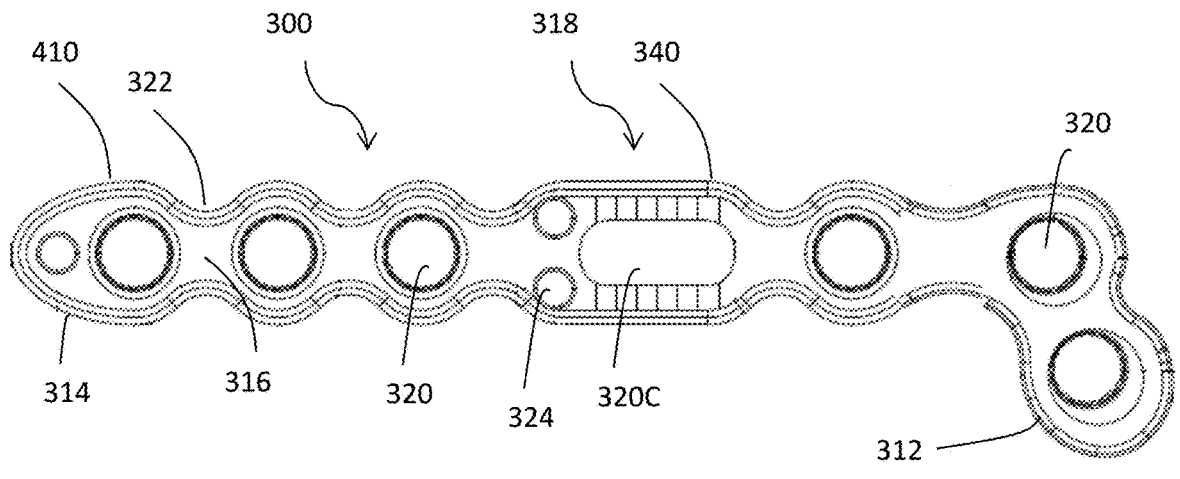
FIG. 22 depicts a stabilization system according to one embodiment including an oblique dorsal bone plate.

FIGS. 20-24 depict embodiments of a dorsal stabilization system 300 including bone plates 310, 410 which are configured to sit against the dorsal portion of bone. One or more bone fasteners 320C are configured to be received in the bone plates 310, 410 to secure the plates 310, 410 to the dorsal portion of a bone. Although generally described with reference to the dorsal portion of bone, it will be appreciated that the stabilization system 300 described herein may be used or adapted to be used for the fixation of other bones as well, such as other portions of the identified bones. It should be noted that the same reference numerals are being used for plates 310, 410 because the plates are similar except for their respective first ends 312 which show different opening 320 configurations. FIG. 20 shows an acute configuration and FIG. 22 shows an oblique configuration.

As shown in FIGS. 20-22, the plates 310, 410 each have a body that extends from a first end 312 to a second end 314. The plates 310, 410 each include a top surface 316 and an opposite, bottom surface 318 configured to contact adjacent bone. The top and bottom surfaces 316, 318 are connected by opposite side surfaces extending from the first to second ends 312, 314 of the plate 310. Although the plate 310, 410 are shown having a generally longitudinal body, it will be appreciated that any suitable shape and contouring of the plates may be provided depending on the location and type of fracture to be plated.

The bone plates 310, 410 include one or more openings 320. The openings 320 extend through the plate 310, 410 from the upper surface 316 to the bottom surface 318 and are configured to accept locking fasteners and non-locking fasteners 320C. When using the plates 310, 410 with bone, surgeons may use only locking, only non-locking or a combination of both locking and non-locking fasteners to connect the bone and the plates 310, 410. The openings 320 may be in the form of any of the openings discussed above with respect to the volar distal radial plate system, the dia-meta plate system, and the alternative hole configurations.

Figure 23:
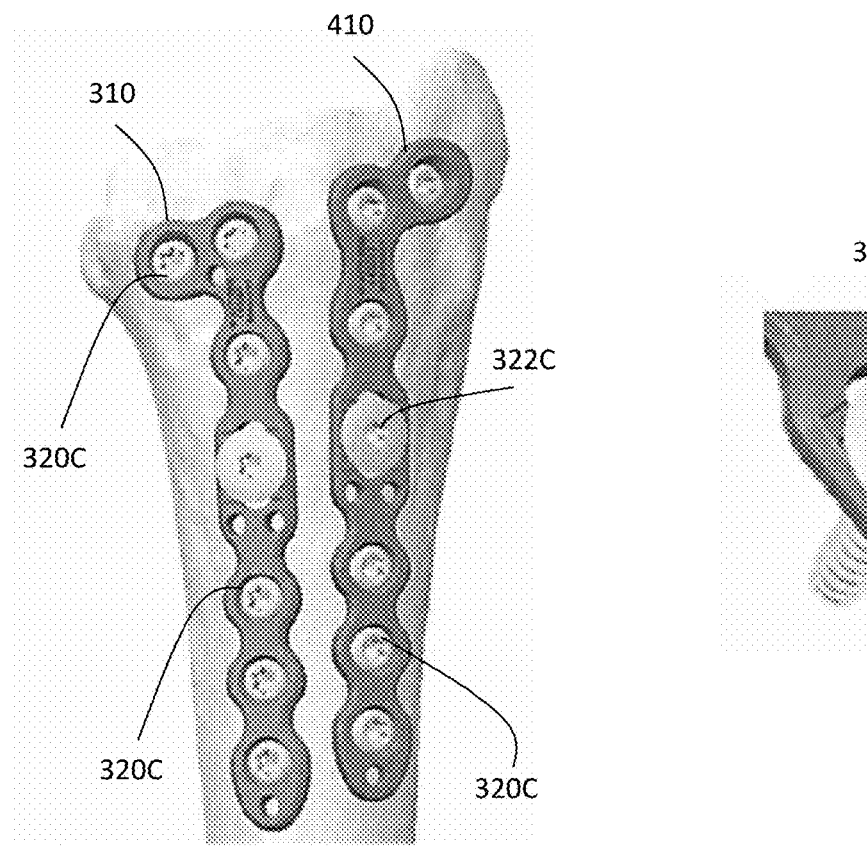
FIG. 23 depicts dorsal bone plates of FIGS. 20 and 22 with fixation screws.
Figure 24:
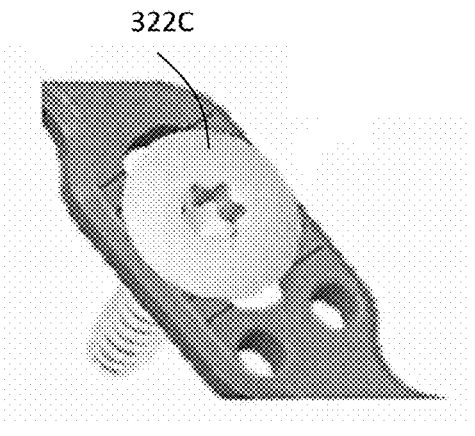
FIG. 24 is a close up view of a portion of the dorsal bone plates of FIGS. 20 and 22.

The plates 310, 410 also include one or more slots 320C present along the elongated portion 340 of the plates 310, 410 and configured to accommodate a sliding fastener 322C, shown in FIGS. 23 and 24. As best seen in FIGS. 20-24, the slot 320C may offer a sliding slot for proximal-distal adjustment of the plates 310, 410 during provisional placement. The slot 320C may allow for proximal adjustment, distal adjustment, and/or medial-lateral adjustment of the plates 310, 410. This allows surgeons to optimally center the plate position along the bone prior to locking screw insertion. The slot 320C may be elongated along a longitudinal axis of the elongated portion 340 as well as elongated, perpendicular to the longitudinal axis, from lateral side to lateral side. The elongated slot 320C may have varying lengths and/or widths. Preferably, the length is greater than the width of the slot 320C. The plates 310, 410 may include etch lines adjacent to slot 320C for more accurate adjustment of the plate 310 when being positioned on bone.

As best seen in FIGS. 20 and 22, plates 310, 410 also may include a plurality of side relief cuts or scalloped edging 322 along the length of the plates 310, 410 which allows the plates 310, 410 to be bent, for example, in three dimensions. The side relief cuts or scalloped edges 322 may be in the form of one or more curves having a widened portion along the sides of the plates 310, 410 and a narrowed portion towards the center of the plates 310, 410. The side relief cuts or scalloped edges 322 may be positioned between consecutive openings 320. The plurality of relief cuts or scalloped edges 322 may form a scalloped or wavy profile along the side edges of the plates 310, 410. As a result, the plates 310, 410 are able to be shaped to a multi-contour surface without warping the openings 320.

The plates 310, 410 may further comprise a plurality of openings 324 configured to receive one or more k-wires (not shown). The k-wire holes 324 may comprise small diameter holes (e.g., having a diameter significantly smaller than the fastener openings 320). The k-wire holes 324 may allow preliminary placement of the plates 310, 410 against the bone and/or to aid in reduction of the fracture.

Lateral Plate

Figure 25:
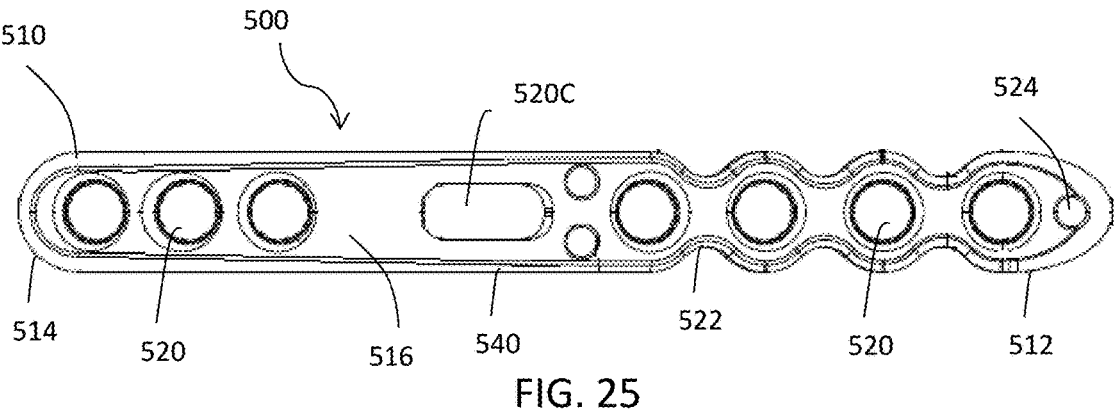
FIG. 25 depicts a stabilization system according to one embodiment including a lateral bone plate.
Figure 26:
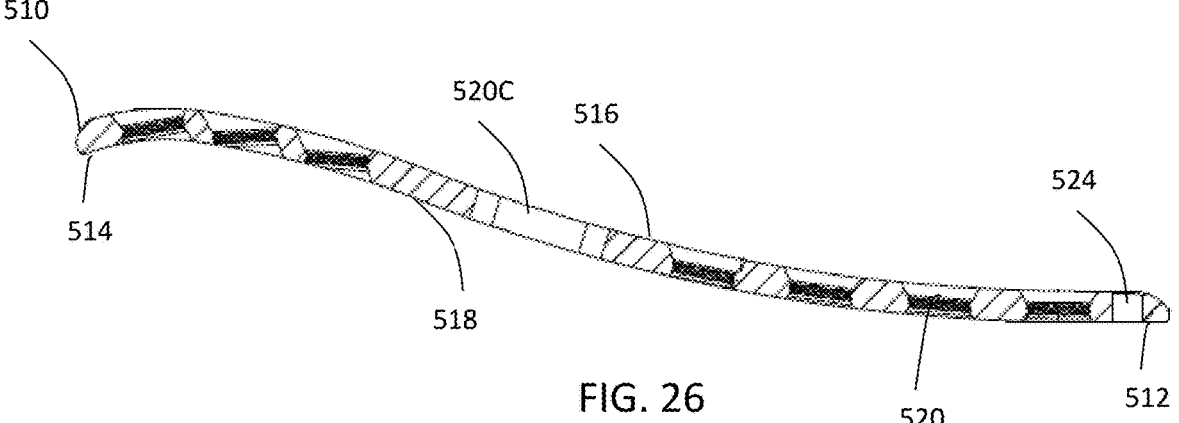
FIG. 26 is a cross sectional view of the lateral bone plate of FIG. 25.
Figure 27:
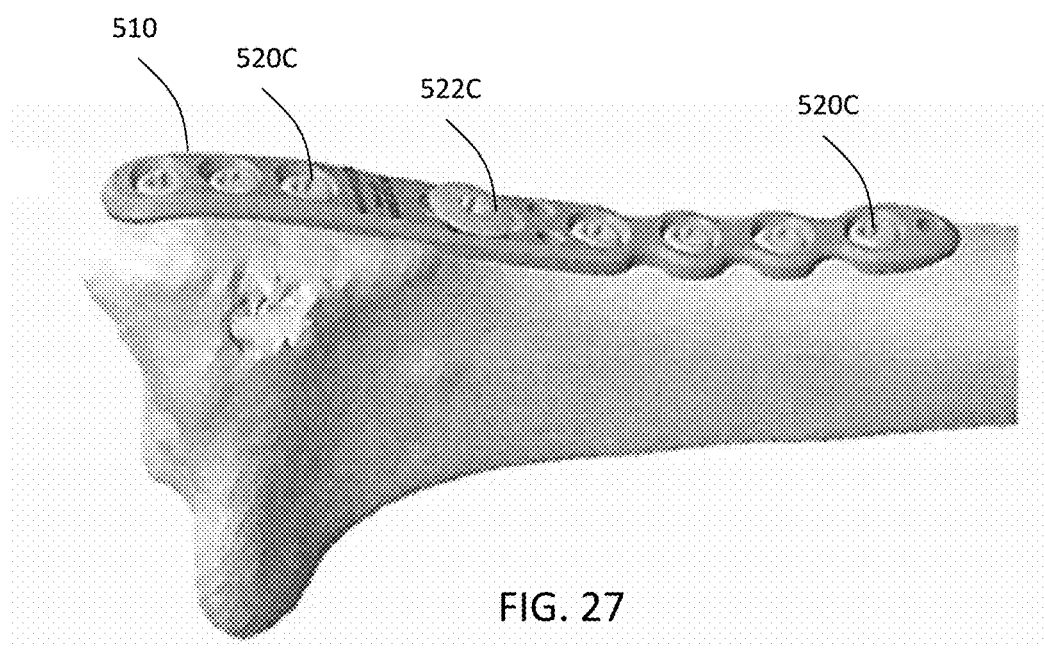
FIG. 27 depicts the lateral bone plate of FIG. 25 with fixation screws.

FIGS. 25-27 depict embodiments of a lateral stabilization system 500 including bone plate 510 which is configured to sit against the lateral portion of bone to address fractures on the side of the radius. One or more bone fasteners 520C are configured to be received in the bone plate 510 to secure the plate 510 to the lateral portion of a radius of a bone. Although generally described with reference to the lateral portion of the radius of the bone, it will be appreciated that the stabilization system 500 described herein may be used or adapted to be used for the fixation of other bones, such as long bones, as well as other portions of the identified bones.

The plate 510 has a body that extends from a first end 512 to a second end 514. The plate 510 includes a top surface 516 and an opposite, bottom surface 518 configured to contact adjacent bone. The top and bottom surfaces 516, 518 are connected by opposite side surfaces extending from the first to second ends 512, 514 of the plate 510. Although the plate 510 is shown having a generally longitudinal body, that contours or radius upwardly to accommodate distal radius bony anatomy, it will be appreciated that any suitable shape and contouring of the plates may be provided depending on the location and type of fracture to be plated.

The bone plate 510 includes one or more openings 520. The openings 520 extend through the plate 510 from the upper surface 516 to the bottom surface 518 and are configured to accept locking fasteners and non-locking fasteners 520C. When using the plate 510 with bone, surgeons may use only locking, only non-locking or a combination of both locking and non-locking fasteners to connect the bone and the plate 510. The openings 520 may be in the form of any of the openings discussed above with respect to the volar distal radial plate system, the dia-meta plate system, the dorsal plates and the alternative hole configurations.

The plate 510 also includes one or more slots 520C present along the elongated portion 540 of the plate 510 and configured to accommodate a sliding fastener 522C, shown in FIG. 27. As best seen in FIGS. 25-26, the slot 520C may offer a sliding slot for proximal-distal adjustment of the plate 510 during provisional placement. The slot 520C may allow for proximal adjustment, distal adjustment, and/or medial-lateral adjustment of the plate 510. This allows surgeons to optimally center the plate position along the bone prior to locking screw insertion. The slot 520C may be elongated along a longitudinal axis of the elongated portion 540 as well as elongated, perpendicular to the longitudinal axis, from lateral side to lateral side. The elongated slot 520C may have varying lengths and/or widths. Preferably, the length is greater than the width of the slot 520C. The plate 510 may include etch lines adjacent to slot 520C for more accurate adjustment of the plate 510 when being positioned on bone.

As best seen in FIGS. 25 and 27, plate 510 also may include a plurality of side relief cuts or scalloped edging 522 along a portion of the length of the plate 510 which allows that portion of the plate 510 to be bent, for example, in three dimensions. The side relief cuts or scalloped edges 522 may be in the form of one or more curves having a widened portion along the sides of the plate 510 and a narrowed portion towards the center of the plate 510. The side relief cuts or scalloped edges 522 may be positioned between consecutive openings 520. The plurality of relief cuts or scalloped edges 522 may form a scalloped or wavy profile along the side edges of the plate 510. As a result, a portion of the plate 510 is able to be shaped to a multi-contour surface without warping the openings 520.

The plate 510 may further comprise a plurality of openings 524 configured to receive one or more k-wires (not shown). The k-wire holes 524 may comprise small diameter holes (e.g., having a diameter significantly smaller than the fastener openings 520). The k-wire holes 524 may allow preliminary placement of the plate 519 against the bone and/or to aid in reduction of the fracture.

Bridge Plate

FIG. 28 depicts an embodiment of a stabilization system 600 including bone plate 610 which acts as an internal fixator for high energy comminuted distal radius fractures. The plate 610 is placed dorsally and extends from the third or second metacarpal to approximately a third to half way down the radius. One or more bone fasteners are configured to be received in the bone plate 610 to secure the plate 610 to the desired portions of bone. Although generally described with reference to the radius and metacarpals, it will be appreciated that the stabilization system 600 described herein may be used or adapted to be used for the fixation of other bones, such as long bones, as well as other portions of the identified bones.

The plate 610 has a body that extends from a first end 612 to a second end 614. The plate 610 includes a top surface 616 and an opposite, bottom surface 618 configured to contact adjacent bone. The top and bottom surfaces 616, 618 are connected by opposite side surfaces extending from the first to second ends 612, 614 of the plate 610. Although the plate 610 is shown having a generally longitudinal body that is generally planar, it will be appreciated that any suitable shape and contouring of the plates may be provided depending on the location and type of fracture to be plated.

The bone plate 610 includes one or more openings 620. The openings 620, which are located proximate the first end 612 and the second end 614, extend through the plate 610 from the upper surface 616 to the bottom surface 618 and are configured to accept locking fasteners and non-locking fasteners. When using the plate 610 with bone, surgeons may use only locking, only non-locking or a combination of both locking and non-locking fasteners to connect the bone and the plate 610. The openings 620 may be in the form of any of the openings discussed above with respect to the volar distal radial plate system, the dia-meta plate system, the dorsal plates, the lateral plates and the alternative hole configurations.

Lunate Facet Hook Plate

Figure 31:
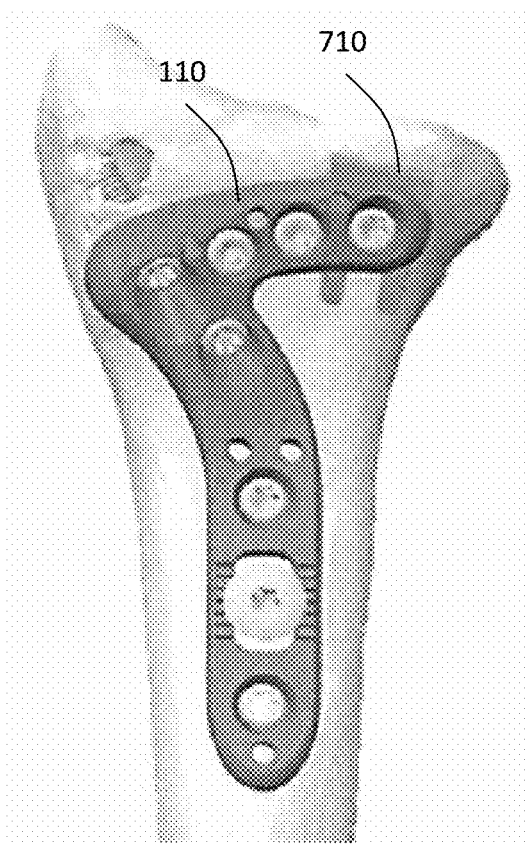
FIG. 31 depicts the volar distal radius plate of FIG. 1 used with the lunate facet hook plate of FIG. 30.

FIGS. 29-31 depicts an embodiment of a stabilization system 700 including hook plate 710 which is designed for fracture patterns that involve the volar ulnar corner of the distal radius. The plate 710 may be used as a stand-alone stabilization plate or may be used in combination with a volar distal radius plate 110, as shown in FIG. 31.

When the plate 710 is used alone, the hooks 712 of the plate are embedded or tapped into bone to prevent the shifting of the plate in a lateral or medial direction. It is contemplated that there may one, two, or more hooks 712. The plate 710 also includes an opening 720 to receive a fixation screw 714, which may aid in further fixation of the plate 710 the bone and the fracture site.

When the plate 710 is used with the volar distal radius plate, the plate 710 is configured and dimensioned such that is can be slidably placed under a pre-positioned volar distal radius plate 110. The opening 720 will align with an opening 120 on the volar distal radius plate 110 such that a fastener will pass through the opening 120 on the volar distal radius plate 110 and the opening 720 on the plate 710. The opening 720 can accept a locking screw or a non-locking screw.

Figure 32:
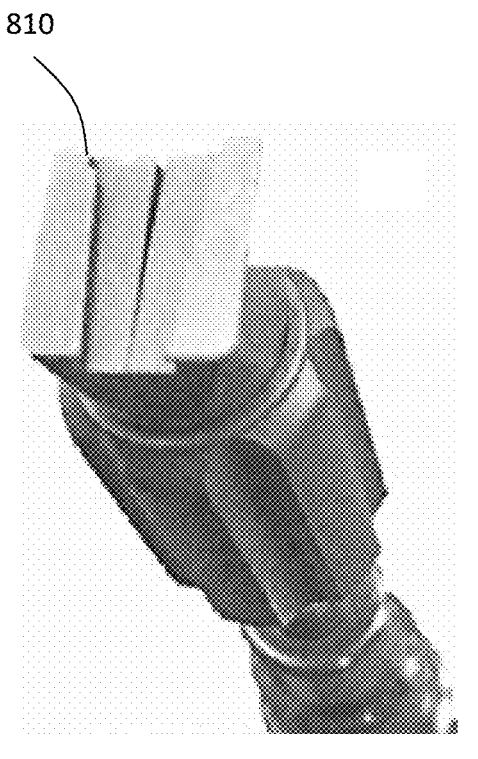
FIGS. 32 and 33 depict a lunate facet hook plate reduction instrument.
Figure 33:
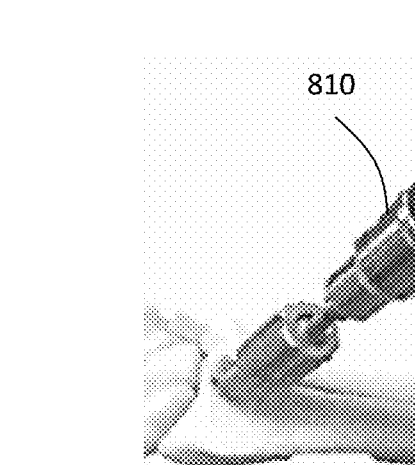

FIGS. 32 and 33 show a lunate facet hook plate reduction instrument 810. The instrument is capable of being connected to any quick connect handle known in the industry, such as the AO quick-connect handle. The reduction instrument 810 utilizes a two-piece contact surface that is capable of capturing a lunate facet hook plate and releasing the hook plate when it is positioned in the desired location and orientation.

Figures 34, 35:
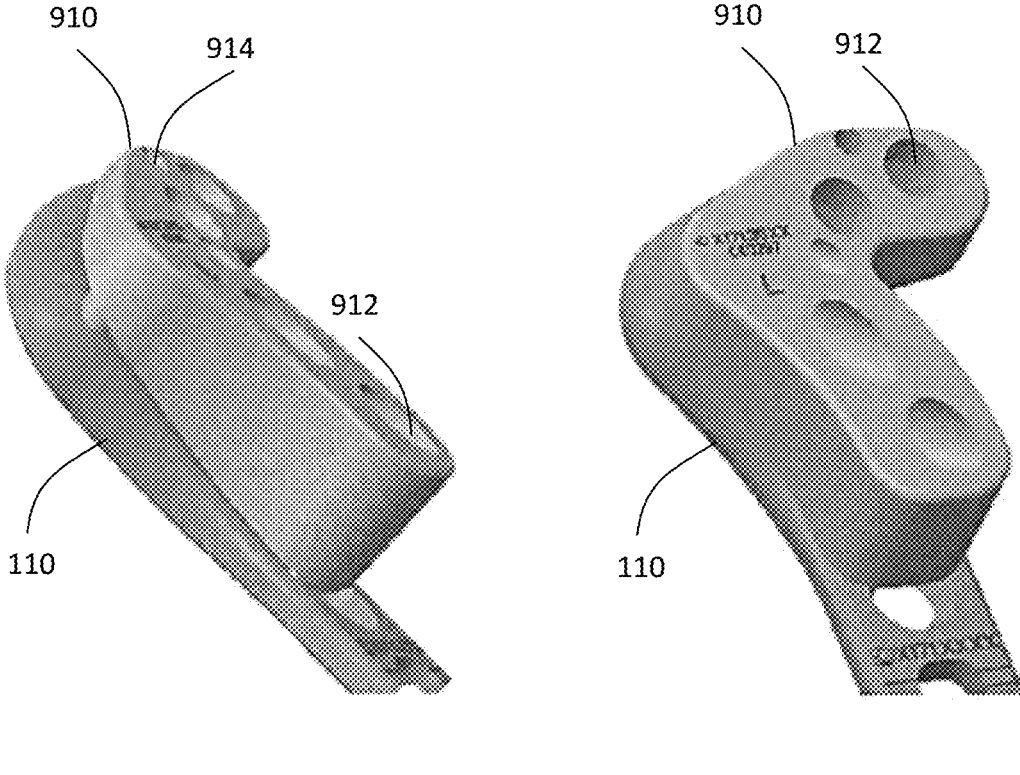
FIGS. 34 and 35 depict a backpack drill guide for use with at least the volar distal radius plates of FIG. 1.

FIGS. 34 and 35 depict a drill guide 910 that can be attached to second end 114 of the volar distal radius plate 110. The drill guide 910 may include a plurality of cannulated openings 912 which correspond to each of the respective openings 120 in the plate 110. The drill guide 910 openings 912 may be configured in order to drill the pilot holes at the appropriate trajectories for each opening 120, and subsequently receive the respective fasteners at the correct trajectories. The drill guide 910 may also include a plurality of k-wire openings 914 which match with the k-wire openings in the plate 110. The drill guide 910 may be secured to the plate 110 with one or more fasteners or may be secured to the plate 110 through an integrated connection system such as a thumb screw, an interference fit, etc. The fastener may thread into the plate 110 or otherwise temporarily secure the drill guide 910 to the plate 110. The drill guide 910 may be pre-assembled to the plate 110 or may be attached at any other suitable time before or during the surgery. The fastener may be secured, for example, in the operating room, via thumb or hexalobular fastener, to attach the drill guide 910 to the plate 110. After the pilot holes are drilled, the drill guide 910 may then be removed and the fasteners positioned through the respective openings 120. The drill guide 910 may be relatively slim in thickness, for example, not protruding more than 10 mm above the plate 110, to prevent impinging on soft tissue.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. A radius bone plate for a lateral side of a radius bone, the radius bone plate comprising:

a proximal portion and a distal portion extending from the proximal portion, the two portions defining the radius bone plate and a longitudinal axis;

wherein the radius bone plate extends from a proximal end to a distal end and includes a top surface and a bottom surface configured to contact the lateral side of the radius bone, opposite side surfaces connecting the top and bottom surfaces, the distal portion being curved upwardly to accommodate a distal radius bony anatomy;

the distal portion including:

an elongate two-axis slot configured to accommodate a sliding fastener for proximal-distal and lateral adjustment of the radius bone plate; and a plurality of locking holes for receiving bone fasteners and positioned distally of the two-axis slot;

the proximal portion including:

a plurality of bone fastener holes; and a plurality of side relief cuts positioned between consecutive bone fastener holes to form a wavy profile along the side surfaces of the proximal portion so as to allow lateral adjustment of the proximal portion to minimize warping of the bone fastener holes.

2. The radius bone plate of claim 1, wherein each of the locking holes of the distal portion includes:

a conical tapered surface for clearance of a bone fastener head during an off-angle insertion;

a thread forming portion disposed below the conical tapered surface and configured to form a thread for the bone fastener;

a tapered surface extending below the thread forming portion for providing clearance for a shank of the bone fastener.

3. The radius bone plate of claim 2, wherein the thread forming portion includes at least one thread forming ring extending inwardly toward a center of the locking hole.

4. The radius bone plate of claim 2, wherein the thread forming portion includes:

a first concentric ring extending inwardly toward a center of the locking hole;

a second concentric ring extending inwardly toward the center of the locking hole and disposed below the first concentric ring.

5. The radius bone plate of claim 4, wherein the first concentric ring extends further toward the center of the locking hole than the second concentric ring.

6. The radius bone plate of claim 1, wherein the distal portion includes two k-wire holes disposed proximally of the two-axis slot and disposed on opposite sides of the longitudinal axis.

7. The radius bone plate of claim 1, wherein the proximal portion includes a k-wire hole disposed proximally of the most proximal one of the bone fastener holes.

8. The radius bone plate of claim 1, wherein the radius bone plate is made of softer material than Cobalt Chromium alloy.

9. A bone plate for a lateral side of a radius bone, the radius bone plate comprising:

a proximal portion and a distal portion extending from the proximal portion, the two portions defining the radius bone plate and a longitudinal axis;

wherein the radius bone plate extends from a proximal end to a distal end and includes a top surface and a bottom surface configured to contact the lateral side of the radius bone, opposite side surfaces connecting the top and bottom surfaces, the distal portion being curved upwardly to accommodate a distal radius bony anatomy;

the distal portion including:

an elongate two-axis slot lying on the longitudinal axis and configured to accommodate a sliding fastener for proximal-distal and lateral adjustment of the radius bone plate; and a plurality of locking holes all lying on the longitudinal axis for receiving bone fasteners and positioned distally of the two-axis slot;

the proximal portion including:

a plurality of bone fastener holes lying on the longitudinal axis; and a plurality of side relief cuts positioned between consecutive bone fastener holes to form a wavy profile along the side surfaces of the proximal portion so as to allow lateral adjustment of the proximal portion to minimize warping of the bone fastener holes.

10. The radius bone plate of claim 9, wherein each of the locking holes of the distal portion includes:

a conical tapered surface for clearance of a bone fastener head during an off-angle insertion;

a thread forming portion disposed below the conical tapered surface and configured to form a thread for the bone fastener;

a tapered surface extending below the thread forming portion for providing clearance for a shank of the bone fastener.

11. The radius bone plate of claim 10, wherein the thread forming portion includes at least one thread forming ring extending inwardly toward a center of the locking hole.

12. The radius bone plate of claim 10, wherein the thread forming portion includes:

a first concentric ring extending inwardly toward a center of the locking hole;

a second concentric ring extending inwardly toward the center of the locking hole and disposed below the first concentric ring.

13. The radius bone plate of claim 12, wherein the first concentric ring extends further toward the center of the locking hole than the second concentric ring.

14. The radius bone plate of claim 9, wherein the distal portion includes two k-wire holes disposed proximally of the two-axis slot and disposed on opposite sides of the longitudinal axis.

15. The radius bone plate of claim 9, wherein the proximal portion includes a k-wire hole disposed proximally of the most proximal one of the bone fastener holes.

16. The radius bone plate of claim 9, wherein the radius bone plate is made of softer material than Cobalt Chromium alloy.

17. The radius bone plate of claim 9, wherein a center of all of the locking holes, the two-axis slot and the bone fastener holes lie on the longitudinal axis.

* * * * *